（12）United States Patent
Ferree

(10) Patent No.: US 8,821,549 B2
(45) Date of Patent: Sep. 2, 2014

(54) METHODS AND APPARATUS FOR ANULUS REPAIR

(75) Inventor: Bret A. Ferree, Cincinnati, OH (US)

(73) Assignee: Anova Corporation, Summit, NJ (US)

( * ) Notice: Subject to any disclaimer, the term of this patent is extended or adjusted under 35 U.S.C. 154(b) by 31 days.

(21) Appl. No.: 13/128,417

(22) PCT Filed: Nov. 25, 2009

(86) PCT No.: PCT/US2009/065954
§ 371 (c)(1),
(2), (4) Date: May 10, 2011

(87) PCT Pub. No.: WO2010/062971
PCT Pub. Date: Jun. 3, 2010

(65) Prior Publication Data
US 2011/0218573 A1 Sep. 8, 2011

Related U.S. Application Data

(63) Continuation-in-part of application No. 12/263,753, filed on Nov. 3, 2008, now abandoned, which is a continuation-in-part of application No. 11/811,751, filed on Jun. 12, 2007, now Pat. No. 8,075,619.

(60) Provisional application No. 61/118,246, filed on Nov. 26, 2008, provisional application No. 60/813,232, filed on Jun. 13, 2006, provisional application No. 60/847,649, filed on Sep. 26, 2006, provisional application No. 60/984,657, filed on Nov. 1, 2007.

(51) Int. Cl.
A61B 17/70 (2006.01)

(52) U.S. Cl.
USPC .......................................... 606/263; 606/321

(58) Field of Classification Search
USPC .................................................. 606/263, 321
See application file for complete search history.

(56) References Cited

U.S. PATENT DOCUMENTS

| 3,867,728 | A | 2/1975 | Stubstad et al. |
| 3,875,595 | A | 4/1975 | Froning |
| 4,349,921 | A | 9/1982 | Kuntz |
| 4,413,359 | A | 11/1983 | Akiyama et al. |
| 4,502,161 | A | 3/1985 | Wall |
| 4,512,338 | A | 4/1985 | Balko et al. |
| 4,532,926 | A | 8/1985 | O'Holla |
| 4,585,458 | A | 4/1986 | Kurland |
| 4,663,358 | A | 5/1987 | Hyon et al. |
| 4,665,906 | A | 5/1987 | Jervis |
| 4,741,330 | A | 5/1988 | Hayhurst |
| 4,744,364 | A | 5/1988 | Kensey |
| 4,772,287 | A | 9/1988 | Ray et al. |

(Continued)

Primary Examiner — Jan Christopher Merene
(74) Attorney, Agent, or Firm — Pandiscio & Pandiscio

(57) ABSTRACT

Apparatus, systems and methods are used to repair, reconstruct and/or replace spinal features. A flexible longitudinal fixation component such a suture is passed around or through a portion of a spine, with the end sections of the component either being attached to one another or coupled to at least one bone implant. The bone implant may be a bone anchor or may form part of a pedicle screw assembly. The flexible longitudinal fixation component may pass through an anulus fibrosis (AF) and at least one intra-aperture component situated within a void or defect in an AF. The intra-aperture component may be composed of a porous mesh, allograft tissue or xenograft tissue. The intra-aperture component preferably includes one or more proximal-to-distal channels facilitating the intentional initial passage of nucleus pulposis (NP) tissue while preventing the extrusion of the NP long term.

14 Claims, 29 Drawing Sheets

(56) References Cited

U.S. PATENT DOCUMENTS

| | | | |
|---|---|---|---|
| 4,781,190 A | 11/1988 | Lee | |
| 4,798,205 A | 1/1989 | Bonomo et al. | |
| 4,834,757 A | 5/1989 | Brantigan | |
| 4,852,568 A | 8/1989 | Kensey | |
| 4,863,477 A | 9/1989 | Monson | |
| 4,873,976 A | 10/1989 | Schreiber | |
| 4,890,612 A | 1/1990 | Kensey | |
| 4,904,260 A | 2/1990 | Ray et al. | |
| 4,911,718 A | 3/1990 | Lee et al. | |
| 4,917,704 A | 4/1990 | Frey et al. | |
| 4,932,969 A | 6/1990 | Frey et al. | |
| 4,946,378 A | 8/1990 | Hirayama et al. | |
| 4,955,908 A | 9/1990 | Frey et al. | |
| 5,002,576 A | 3/1991 | Fuhrmann et al. | |
| 5,015,255 A | 5/1991 | Kuslich | |
| 5,021,059 A | 6/1991 | Kensey et al. | |
| 5,035,716 A | 7/1991 | Downey | |
| 5,047,055 A | 9/1991 | Bao et al. | |
| 5,053,046 A | 10/1991 | Janese | |
| 5,059,206 A | 10/1991 | Winters | |
| 5,061,274 A | 10/1991 | Kensey | |
| 5,071,437 A | 12/1991 | Steffee | |
| 5,100,422 A | 3/1992 | Berguer et al. | |
| 5,108,438 A | 4/1992 | Stone | |
| 5,116,357 A | 5/1992 | Eberbach | |
| 5,122,155 A | 6/1992 | Eberbach | |
| 5,123,926 A | 6/1992 | Pisharodi | |
| 5,141,515 A | 8/1992 | Eberbach | |
| 5,147,374 A | 9/1992 | Fernandez | |
| 5,171,259 A | 12/1992 | Inoue | |
| 5,171,278 A | 12/1992 | Pisharodi | |
| 5,171,280 A | 12/1992 | Baumgartner | |
| 5,171,281 A | 12/1992 | Parsons et al. | |
| 5,176,692 A | 1/1993 | Wilk et al. | |
| 5,192,326 A | 3/1993 | Bao et al. | |
| 5,222,974 A | 6/1993 | Kensey et al. | |
| 5,254,133 A | 10/1993 | Seid | |
| 5,258,000 A | 11/1993 | Gianturco | |
| 5,258,043 A | 11/1993 | Stone | |
| 5,269,783 A | 12/1993 | Sander | |
| 5,282,827 A | 2/1994 | Kensey et al. | |
| 5,304,194 A | 4/1994 | Chee et al. | |
| 5,306,311 A | 4/1994 | Stone et al. | |
| 5,312,435 A | 5/1994 | Nash et al. | |
| 5,318,780 A | 6/1994 | Viegas et al. | |
| 5,320,633 A | 6/1994 | Allen et al. | |
| 5,320,644 A | 6/1994 | Baumgartner | |
| 5,342,393 A | 8/1994 | Stack | |
| 5,342,394 A | 8/1994 | Matsuno et al. | |
| 5,356,432 A | 10/1994 | Rutkow et al. | |
| 5,366,460 A | 11/1994 | Eberbach | |
| 5,368,602 A | 11/1994 | de la Torre | |
| 5,370,660 A | 12/1994 | Weinstein et al. | |
| 5,370,697 A | 12/1994 | Baumgartner | |
| 5,376,693 A | 12/1994 | Viegas et al. | |
| 5,383,477 A | 1/1995 | DeMatteis | |
| 5,383,905 A | 1/1995 | Golds et al. | |
| 5,390,683 A | 2/1995 | Pisharodi | |
| 5,397,331 A | 3/1995 | Himpens et al. | |
| 5,397,332 A | 3/1995 | Kammerer et al. | |
| 5,405,360 A | 4/1995 | Tovey | |
| 5,425,772 A | 6/1995 | Brantigan | |
| 5,425,773 A | 6/1995 | Boyd et al. | |
| 5,437,631 A | 8/1995 | Janzen | |
| 5,456,720 A | 10/1995 | Schultz et al. | |
| 5,464,407 A | 11/1995 | McGuire | |
| 5,500,000 A | 3/1996 | Feagin et al. | |
| 5,507,754 A | 4/1996 | Green et al. | |
| 5,514,180 A | 5/1996 | Heggeness et al. | |
| 5,520,700 A | 5/1996 | Beyar et al. | |
| 5,531,759 A | 7/1996 | Kensey et al. | |
| 5,534,028 A | 7/1996 | Bao et al. | |
| 5,534,030 A | 7/1996 | Navarro et al. | |
| 5,540,715 A | 7/1996 | Katsaros et al. | |
| 5,545,178 A | 8/1996 | Kensey et al. | |
| 5,545,229 A | 8/1996 | Parsons et al. | |
| 5,549,617 A | 8/1996 | Green et al. | |
| 5,549,679 A | 8/1996 | Kuslich | |
| 5,556,428 A | 9/1996 | Shah | |
| 5,556,429 A | 9/1996 | Felt | |
| 5,562,689 A | 10/1996 | Green et al. | |
| 5,562,736 A | 10/1996 | Ray et al. | |
| 5,562,738 A | 10/1996 | Boyd et al. | |
| 5,569,252 A | 10/1996 | Justin et al. | |
| 5,571,189 A | 11/1996 | Kuslich | |
| 5,582,616 A | 12/1996 | Bolduc et al. | |
| 5,587,175 A | 12/1996 | Viegas et al. | |
| 5,591,223 A | 1/1997 | Lock et al. | |
| 5,613,974 A | 3/1997 | Andreas et al. | |
| 5,620,012 A | 4/1997 | Benderev et al. | |
| 5,624,463 A | 4/1997 | Stone et al. | |
| 5,626,613 A | 5/1997 | Schmieding | |
| 5,634,931 A | 6/1997 | Kugel | |
| 5,645,084 A | 7/1997 | McKay | |
| 5,645,597 A | 7/1997 | Krapiva | |
| 5,658,343 A | 8/1997 | Hauselmann et al. | |
| 5,662,683 A | 9/1997 | Kay | |
| 5,669,935 A | 9/1997 | Rosenman et al. | |
| 5,674,294 A | 10/1997 | Bainville et al. | |
| 5,674,296 A | 10/1997 | Bryan et al. | |
| 5,676,698 A | 10/1997 | Janzen et al. | |
| 5,676,701 A | 10/1997 | Yuan et al. | |
| 5,681,310 A | 10/1997 | Yuan et al. | |
| 5,681,351 A | 10/1997 | Jamiolkowski et al. | |
| 5,683,465 A | 11/1997 | Shinn et al. | |
| 5,690,674 A | 11/1997 | Diaz | |
| 5,695,525 A | 12/1997 | Mulhauser et al. | |
| 5,702,450 A | 12/1997 | Bisserie | |
| 5,702,451 A | 12/1997 | Biedermann et al. | |
| 5,702,454 A | 12/1997 | Baumgartner | |
| 5,702,462 A | 12/1997 | Oberlander | |
| 5,709,854 A | 1/1998 | Griffith-Cima et al. | |
| 5,716,408 A | 2/1998 | Eldridge et al. | |
| 5,716,409 A | 2/1998 | Debbas | |
| 5,716,413 A | 2/1998 | Walter et al. | |
| 5,716,416 A | 2/1998 | Lin | |
| 5,718,862 A | 2/1998 | Thompson | |
| 5,725,577 A | 3/1998 | Saxon | |
| 5,728,150 A | 3/1998 | McDonald et al. | |
| 5,730,744 A | 3/1998 | Justin et al. | |
| 5,733,337 A | 3/1998 | Carr, Jr. et al. | |
| 5,743,917 A | 4/1998 | Saxon | |
| 5,746,755 A | 5/1998 | Wood et al. | |
| 5,746,765 A | 5/1998 | Kleshinski et al. | |
| 5,766,246 A | 6/1998 | Mulhauser et al. | |
| 5,769,864 A | 6/1998 | Kugel | |
| 5,769,893 A | 6/1998 | Shah | |
| 5,772,661 A | 6/1998 | Michelson | |
| 5,776,183 A | 7/1998 | Kanesaka et al. | |
| 5,782,844 A | 7/1998 | Yoon et al. | |
| 5,785,705 A | 7/1998 | Baker | |
| 5,800,549 A | 9/1998 | Bao et al. | |
| 5,800,550 A | 9/1998 | Sertich | |
| 5,801,033 A | 9/1998 | Hubbell et al. | |
| 5,810,851 A | 9/1998 | Yoon | |
| 5,823,994 A | 10/1998 | Sharkey et al. | |
| 5,824,008 A | 10/1998 | Bolduc et al. | |
| 5,824,082 A | 10/1998 | Brown | |
| 5,824,093 A | 10/1998 | Ray et al. | |
| 5,824,094 A | 10/1998 | Serhan et al. | |
| 5,827,298 A | 10/1998 | Hart et al. | |
| 5,827,328 A | 10/1998 | Buttermann | |
| 5,836,315 A | 11/1998 | Benderev et al. | |
| 5,843,084 A | 12/1998 | Hart et al. | |
| 5,846,261 A | 12/1998 | Kotula et al. | |
| 5,860,425 A | 1/1999 | Benderev et al. | |
| 5,860,977 A | 1/1999 | Zucherman et al. | |
| 5,865,845 A | 2/1999 | Thalgott | |
| 5,865,846 A | 2/1999 | Bryan et al. | |
| 5,879,366 A | 3/1999 | Shaw et al. | |
| 5,888,220 A | 3/1999 | Felt et al. | |
| 5,888,226 A | 3/1999 | Rogozinski | |
| 5,893,889 A | 4/1999 | Harrington | |
| 5,916,225 A | 6/1999 | Kugel | |

(56) References Cited

U.S. PATENT DOCUMENTS

| | | | |
|---|---|---|---|
| 5,919,235 A | 7/1999 | Husson et al. | |
| 5,922,026 A | 7/1999 | Chin | |
| 5,928,284 A | 7/1999 | Mehdizadeh | |
| 5,935,147 A | 8/1999 | Kensey et al. | |
| 5,954,716 A | 9/1999 | Sharkey et al. | |
| 5,954,767 A | 9/1999 | Pajotin et al. | |
| 5,957,939 A | 9/1999 | Heaven et al. | |
| 5,972,000 A | 10/1999 | Beyar et al. | |
| 5,972,007 A | 10/1999 | Sheffield et al. | |
| 5,972,022 A | 10/1999 | Huxel | |
| 5,976,174 A | 11/1999 | Ruiz | |
| 5,976,186 A | 11/1999 | Bao et al. | |
| 5,980,504 A | 11/1999 | Sharkey et al. | |
| 6,001,130 A | 12/1999 | Bryan et al. | |
| 6,007,570 A | 12/1999 | Sharkey et al. | |
| 6,007,575 A | 12/1999 | Samuels | |
| 6,019,793 A | 2/2000 | Perren et al. | |
| 6,024,754 A | 2/2000 | Engelson | |
| 6,027,527 A | 2/2000 | Asano et al. | |
| 6,126,682 A | 10/2000 | Sharkey et al. | |
| 6,140,452 A | 10/2000 | Felt et al. | |
| 6,146,380 A | 11/2000 | Racz et al. | |
| 6,180,848 B1 | 1/2001 | Flament et al. | |
| 6,183,518 B1 | 2/2001 | Ross et al. | |
| 6,206,921 B1 | 3/2001 | Guagliano et al. | |
| 6,224,630 B1 | 5/2001 | Bao et al. | |
| 6,245,107 B1 | 6/2001 | Ferree | |
| 6,248,106 B1 | 6/2001 | Ferree | |
| 6,371,990 B1* | 4/2002 | Ferree | 623/17.16 |
| 6,402,750 B1 | 6/2002 | Atkinson et al. | |
| 6,425,919 B1 | 7/2002 | Lambrecht | |
| 6,428,576 B1 | 8/2002 | Haldimann | |
| 6,436,143 B1 | 8/2002 | Ross et al. | |
| 6,482,235 B1 | 11/2002 | Lambrecht et al. | |
| 6,511,491 B2 | 1/2003 | Grudem et al. | |
| 6,733,531 B1 | 5/2004 | Trieu | |
| 6,878,167 B2 | 4/2005 | Ferree | |
| 7,004,970 B2 | 2/2006 | Cauthen, III et al. | |
| 7,201,774 B2 | 4/2007 | Ferree | |
| 7,338,525 B2 | 3/2008 | Ferree | |
| 7,445,634 B2* | 11/2008 | Trieu | 623/17.11 |
| 7,922,768 B2* | 4/2011 | Cauthen et al. | 623/17.16 |
| 7,947,080 B2 | 5/2011 | Ferree | |
| 8,109,978 B2 | 2/2012 | Ferree | |
| 8,128,698 B2* | 3/2012 | Bentley et al. | 623/17.11 |
| 2002/0120270 A1* | 8/2002 | Trieu et al. | 606/61 |
| 2002/0123750 A1 | 9/2002 | Eisermann et al. | |
| 2002/0198599 A1 | 12/2002 | Haldimann | |
| 2003/0040796 A1* | 2/2003 | Ferree | 623/17.11 |
| 2003/0074075 A1 | 4/2003 | Thomas et al. | |
| 2003/0114930 A1 | 6/2003 | Lim et al. | |
| 2003/0158604 A1* | 8/2003 | Cauthen et al. | 623/17.16 |
| 2004/0059418 A1* | 3/2004 | McKay et al. | 623/17.16 |
| 2004/0186573 A1* | 9/2004 | Ferree | 623/17.11 |
| 2004/0260397 A1 | 12/2004 | Lambrecht et al. | |
| 2005/0125071 A1 | 6/2005 | Nahleili | |
| 2005/0143826 A1* | 6/2005 | Zucherman et al. | 623/17.16 |
| 2006/0217747 A1 | 9/2006 | Ferree | |
| 2006/0247785 A1* | 11/2006 | Gorensek et al. | 623/17.16 |
| 2007/0067040 A1* | 3/2007 | Ferree | 623/17.16 |
| 2007/0135920 A1* | 6/2007 | Ferree | 623/17.11 |
| 2007/0167951 A1 | 7/2007 | Ainsworth et al. | |
| 2007/0276494 A1 | 11/2007 | Ferree | |
| 2007/0288040 A1 | 12/2007 | Ferree | |
| 2008/0004702 A1* | 1/2008 | Denoziere | 623/17.13 |
| 2008/0177298 A1 | 7/2008 | Zucherman et al. | |
| 2010/0016889 A1* | 1/2010 | Ferree | 606/228 |
| 2011/0034975 A1 | 2/2011 | Ferree | |

* cited by examiner

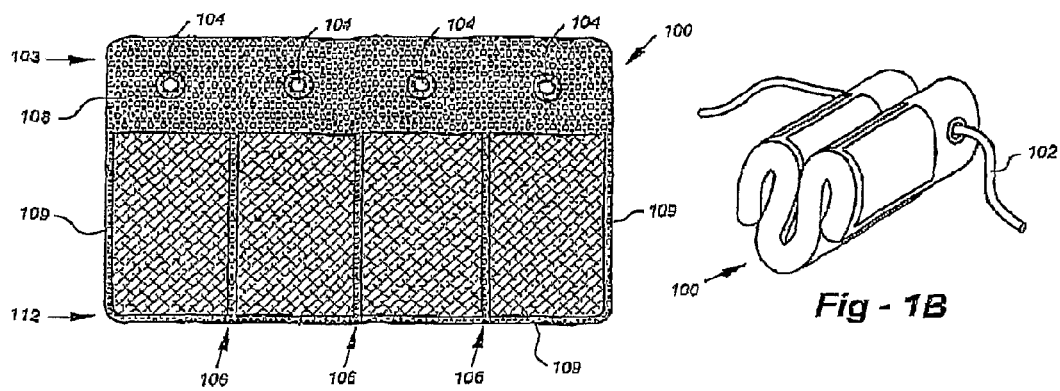
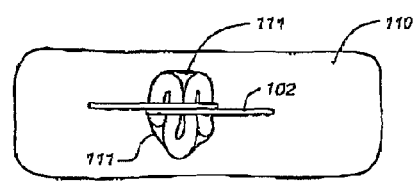
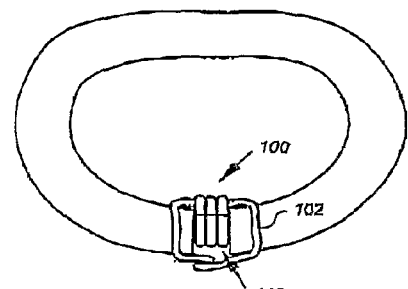
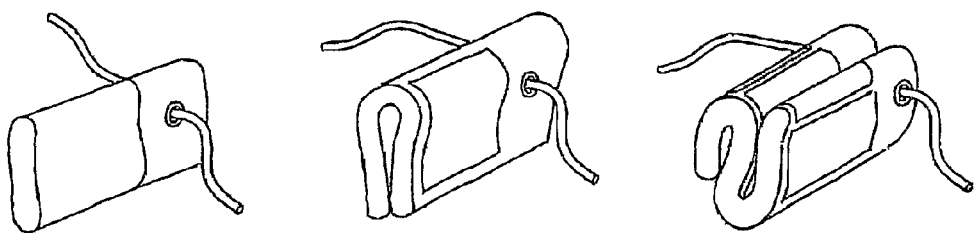
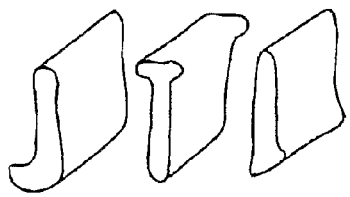

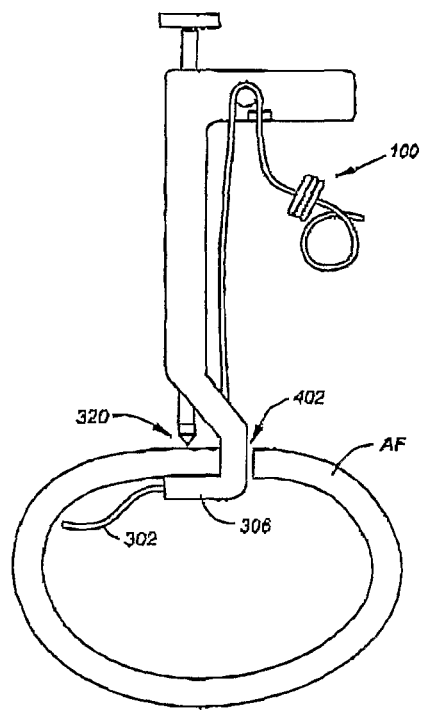 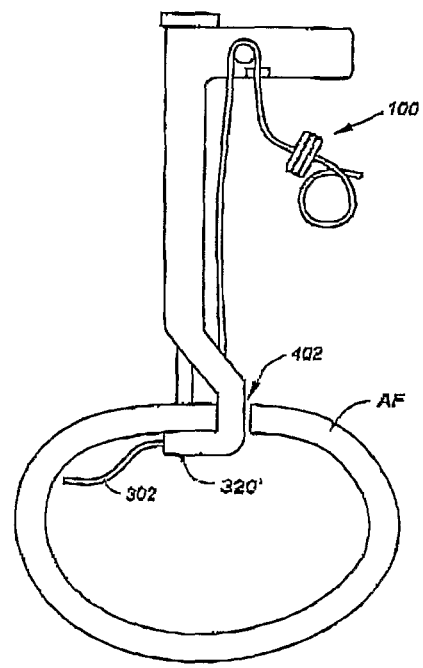
*Fig - 4A*  *Fig - 4B*
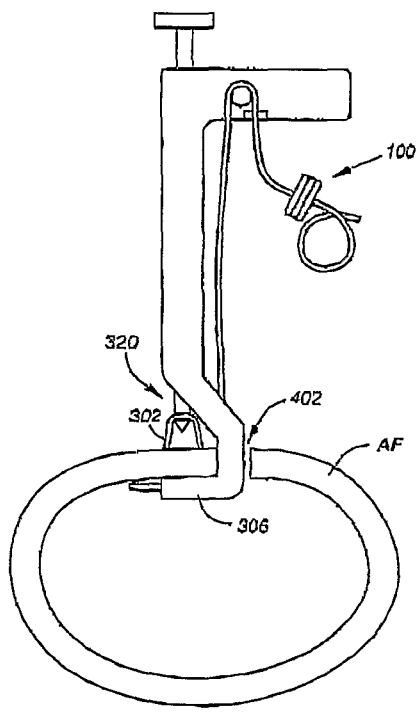 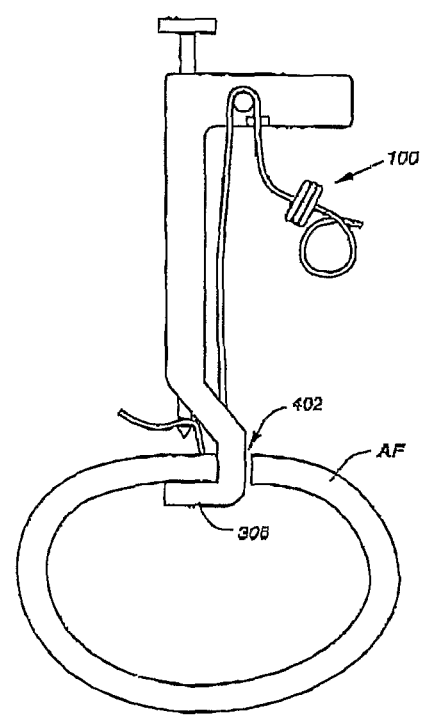
*Fig - 4C*  *Fig - 4D*

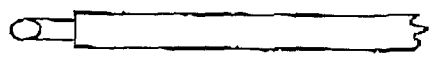
Fig - 11C    Fig - 11D
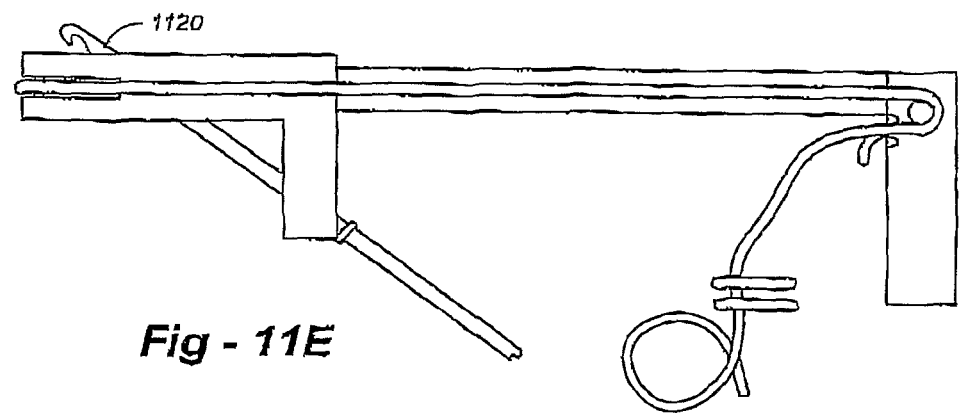
Fig - 11E
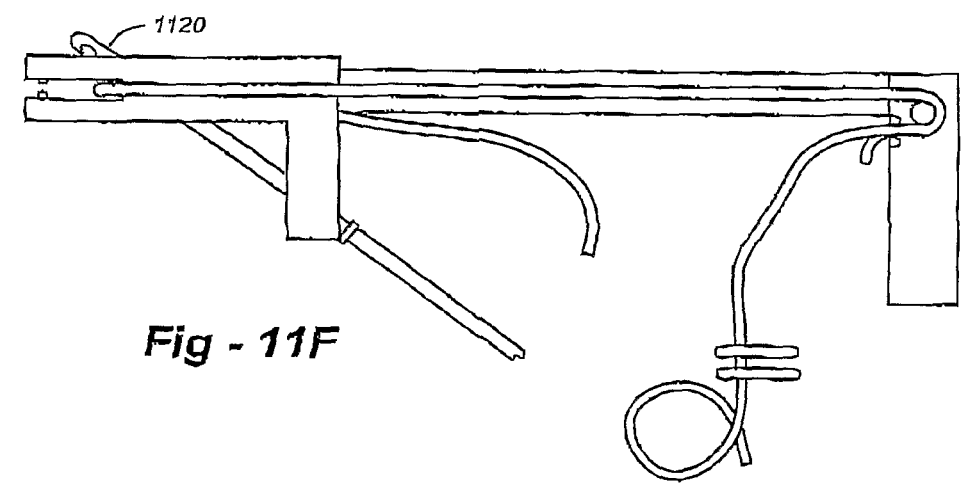
Fig - 11F
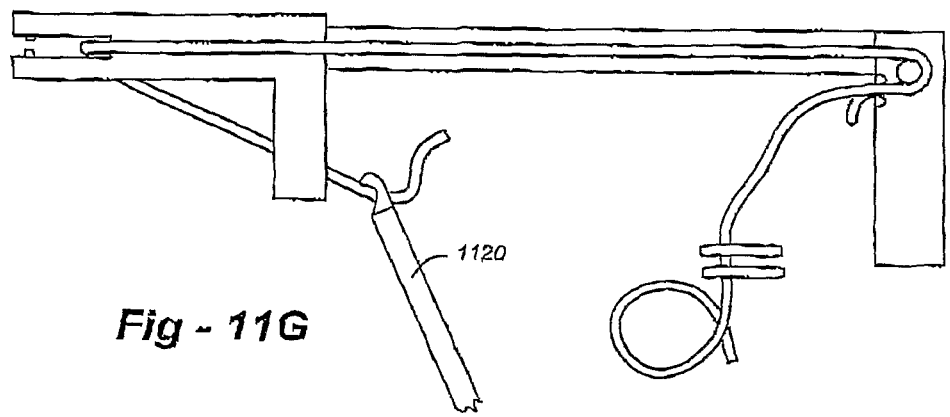
Fig - 11G

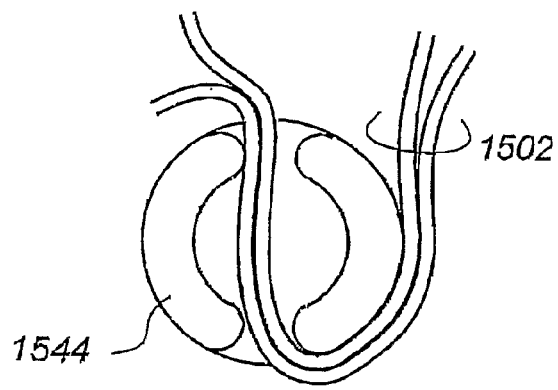
Fig - 15C
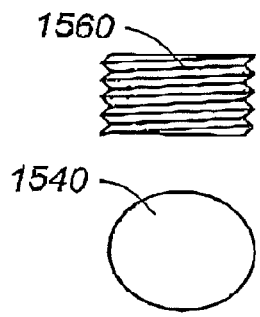
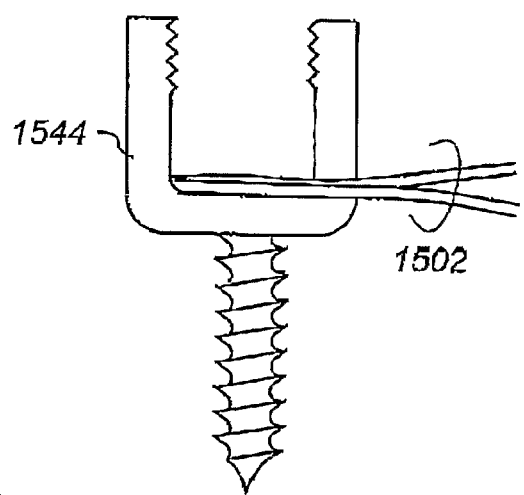
Fig - 15D
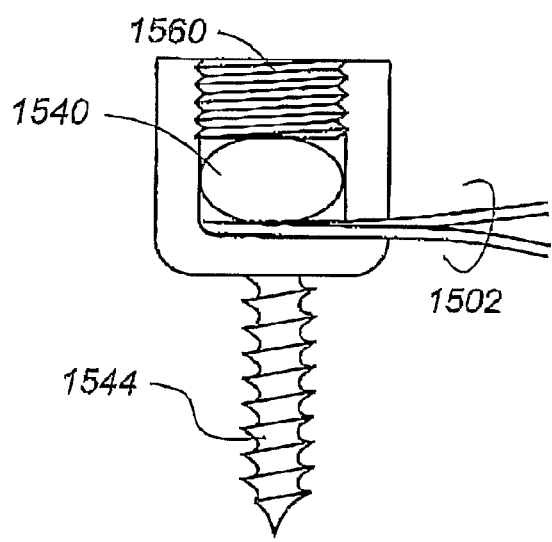
Fig - 15E

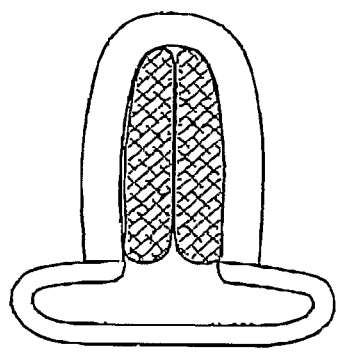
*Fig - 17E*
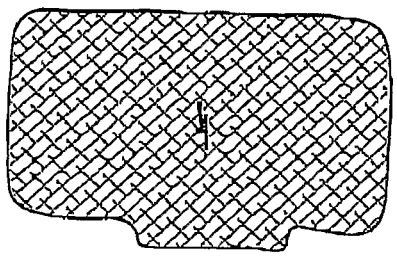
*Fig - 17F*
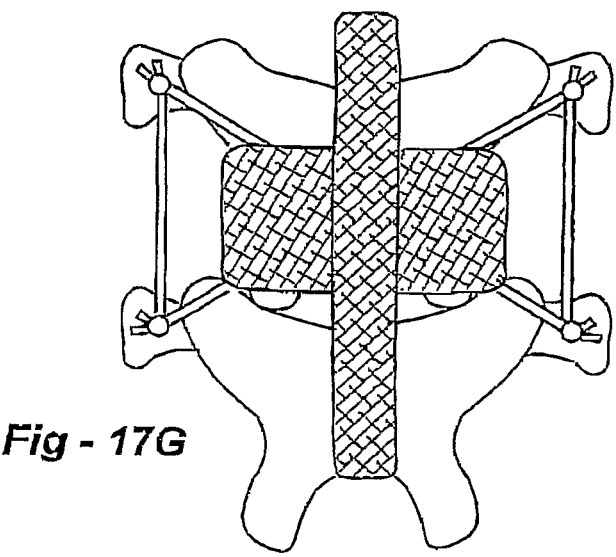
*Fig - 17G*
*Fig - 17H*
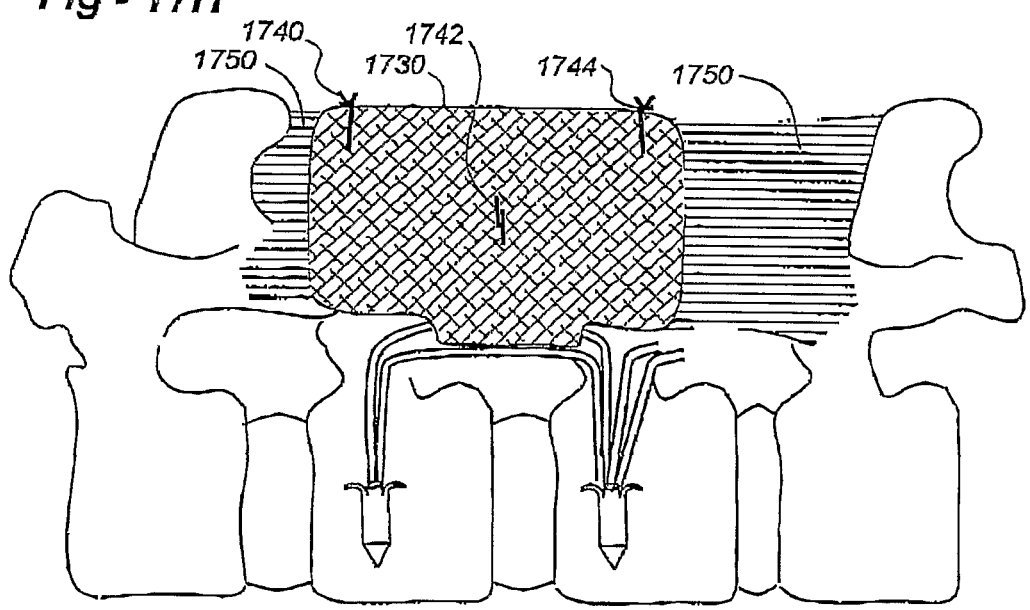

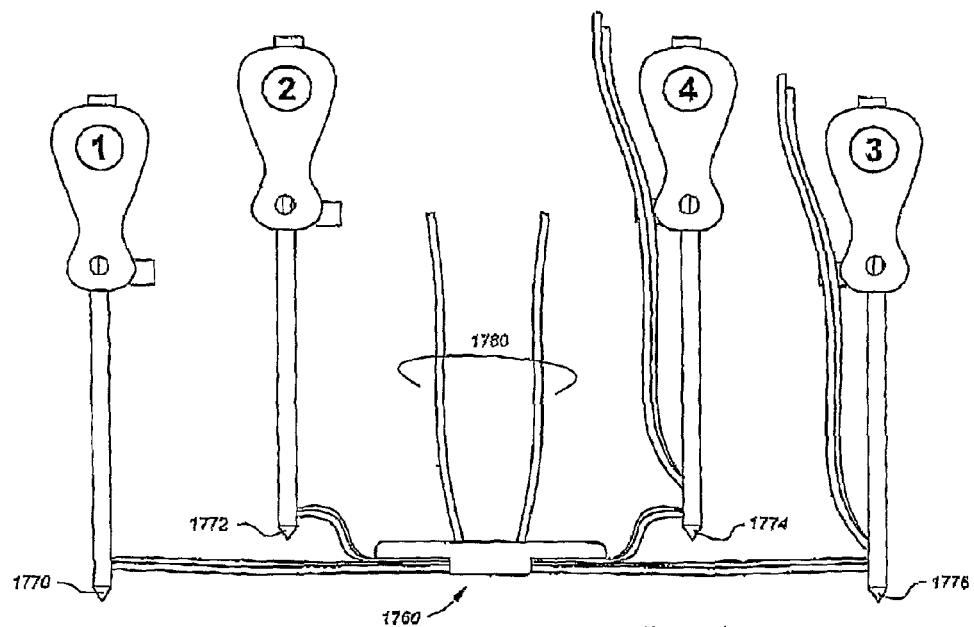
Fig - 17I
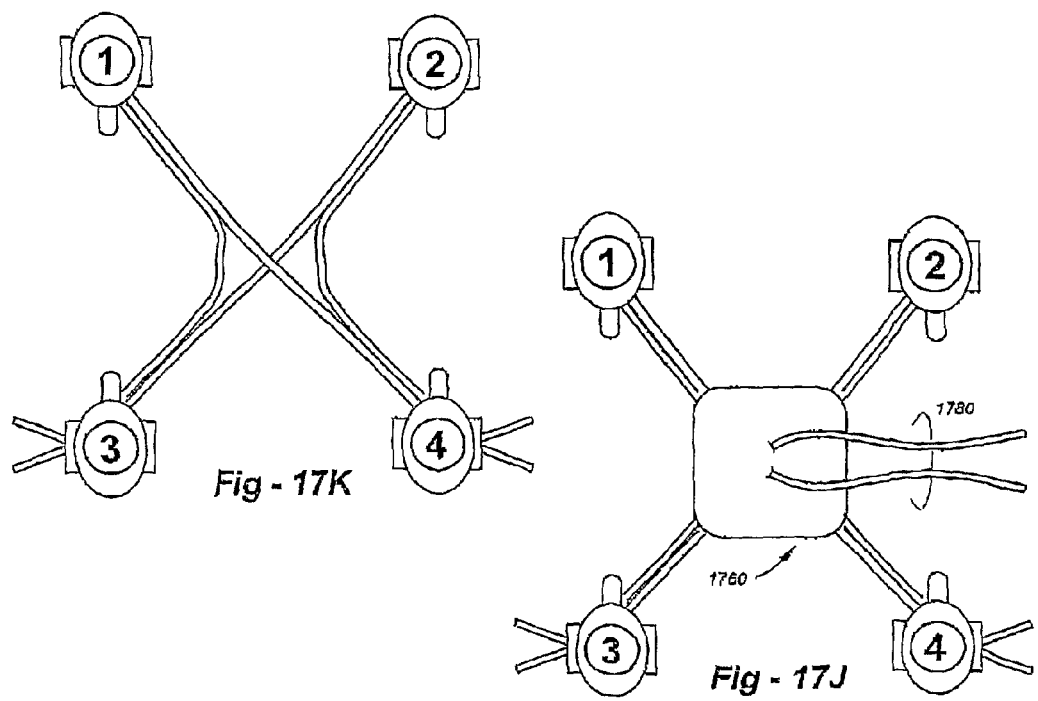
Fig - 17K
Fig - 17J

METHODS AND APPARATUS FOR ANULUS REPAIR

REFERENCE TO RELATED APPLICATIONS

This application claims priority from U.S. Provisional Patent Application Ser. No. 61/118,246, filed Nov. 26, 2008. This application is also continuation-in-part of U.S. patent application Ser. No. 12/263,753, filed Nov. 3, 2008. The entire content of each application is incorporated herein by reference.

FIELD OF THE INVENTION

This invention relates generally to the treatment of intervertebral disc herniation and degenerative disc disease and, in particular, to apparatus and methods for fortifying and/or replacing disc components such as the anulus fibrosis.

BACKGROUND OF THE INVENTION

The human intervertebral disc is an oval to kidney bean-shaped structure of variable size depending on the location in the spine. The outer portion of the disc is known as the anulus fibrosus (AF, also known as the "anulus fibrosis"). The anulus fibrosus (AF) is made of ten to twenty collagen fiber lamellae. The collagen fibers within a lamella are parallel. Successive lamellae are oriented in alternating directions. About 48 percent of the lamellae are incomplete, but this value varies based upon location and increases with age. On average, the lamellae lie at an angle of 60 degrees with respect to the vertebral axis line, but this too varies depending upon location. The orientation serves to control vertebral motion (one half of the bands tighten to check motion when the vertebra above or below the disc are turned in either direction).

The anulus fibrosus contains the nucleus pulposus (NP). The nucleus pulposus serves to transmit and dampen axial loads. High water content (approximately 70-80 percent) assists the nucleus in this function. The water content has a diurnal variation. The nucleus imbibes water while a person lies recumbent. Nuclear material removed from the body and placed into water will imbibe water swelling to several times its normal size. Activity squeezes fluid from the disc. The nucleus comprises roughly 50 percent of the entire disc. The nucleus contains cells (chondrocytes and fibrocytes) and proteoglycans (chondroitin sulfate and keratin sulfate). The cell density in the nucleus is on the order of 4,000 cells per microliter.

The intervertebral disc changes or "degenerates" with age. As a person ages, the water content of the disc falls from approximately 85 percent at birth to approximately 70 percent in the elderly. The ratio of chondroitin sulfate to keratin sulfate decreases with age, while the ratio of chondroitin 6 sulfate to chondroitin 4 sulfate increases with age. The distinction between the anulus and the nucleus decreases with age. Generally disc degeneration is painless.

Premature or accelerated disc degeneration is known as degenerative disc disease. A large portion of patients suffering from chronic low back pain are thought to have this condition. As the disc degenerates, the nucleus and anulus functions are compromised. The nucleus becomes thinner and less able to handle compression loads. The anulus fibers become redundant as the nucleus shrinks. The redundant anular fibers are less effective in controlling vertebral motion. This disc pathology can result in: 1) bulging of the anulus into the spinal cord or nerves; 2) narrowing of the space between the vertebra where the nerves exit; 3) tears of the anulus as abnormal loads are transmitted to the anulus and the anulus is subjected to excessive motion between vertebra; and 4) disc herniation or extrusion of the nucleus through complete anular tears.

Current surgical treatments for disc degeneration are destructive. One group of procedures, which includes lumbar discectomy, removes the nucleus or a portion of the nucleus. A second group of procedures destroy nuclear material. This group includes Chymopapin (an enzyme) injection, laser discectomy, and thermal therapy (heat treatment to denature proteins). The first two groups of procedures compromise the treated disc. A third group, which includes spinal fusion procedures, either removes the disc or the disc's function by connecting two or more vertebra together with bone. Fusion procedures transmit additional stress to the adjacent discs, which results in premature disc degeneration of the adjacent discs. These destructive procedures lead to acceleration of disc degeneration.

Prosthetic disc replacement offers many advantages. The prosthetic disc attempts to eliminate a patient's pain while preserving the disc's function. Current prosthetic disc implants either replace the nucleus or replace both the nucleus and the anulus. Both types of current procedures remove the degenerated disc component to allow room for the prosthetic component. Although the use of resilient materials has been proposed, the need remains for further improvements in the way in which prosthetic components are incorporated into the disc space to ensure strength and longevity. Such improvements are necessary, since the prosthesis may be subjected to 100,000,000 compression cycles over the life of the implant.

Current nucleus replacements (NRs) may cause lower back pain if too much pressure is applied to the anulus fibrosus. As discussed in U.S. Pat. Nos. 6,878,167 and 7,201,774, the content of each being expressly incorporated herein by reference in their entirety, the posterior portion of the anulus fibrosus has abundant pain fibers.

Herniated nucleus pulposus (HNP) occurs from tears in the anulus fibrosus. The herniated nucleus pulposus often allies pressure on the nerves or spinal cord. Compressed nerves cause back and leg or arm pain. Although a patient's symptoms result primarily from pressure by the nucleus pulposus, the primary pathology lies in the anulus fibrosus.

Surgery for herniated nucleus pulposus, known as microlumbar discectomy (MLD), only addresses the nucleus pulposus. The opening in the anulus fibrosus is enlarged during surgery, further weakening the anulus fibrosus. Surgeons also remove generous amounts of the nucleus pulposus to reduce the risk of extruding additional pieces of nucleus pulposus through the defect in the anulus fibrosus. Although microlumbar discectomy decreases or eliminates a patient's leg or arm pain, the procedure damages weakened discs.

SUMMARY OF THE INVENTION

This invention broadly resides in apparatus, systems and methods to repair, reconstruct and/or replace spinal features. The preferred embodiments include a flexible longitudinal fixation component such as suture material passing around or through a portion of a spine, with the end sections of the flexible longitudinal fixation component either being attached to one another or coupled to at least one bone implant. The bone implant may be a bone anchor or may form part of a pedicle screw assembly.

In certain embodiments the flexible longitudinal fixation component passes through an anulus fibrosis (AF) and at least one intra-aperture component situated within a void or defect in an AF. The intra-aperture component may be composed of a porous mesh, allograft tissue or xenograft tissue. The intra-aperture component preferably includes one or more proximal-to-distal channels facilitating the intentional initial passage of nucleus pulposis (NP) tissue while preventing the extrusion of the NP long term. Such channels may be formed by folding the intra-aperture component along one or more proximal-to-distal fold lines, or tube-like structures may be used. Such passageways intentionally facilitate at least the initial the escape of nucleus pulposus tissue through or around the intra-aperture component in response to pressure applied by the upper and lower vertebral bodies.

The invention may be used in the treatment of herniated discs, anular tears of the disc, or disc degeneration, while enabling surgeons to preserve the contained nucleus pulposus. Anulus reconstruction prevents extrusion of the nucleus replacements through holes in the anulus fibrosus. The nucleus replacements and the anulus fibrosus reconstruction prevent excessive pressure on the anulus fibrosus that may cause back or leg pain. The methods and apparatus may be used to treat discs throughout the spine including the cervical, thoracic, and lumbar spines of humans and animals.

The invention also enables surgeons to reconstruct the anulus fibrosus and replace or augment the nucleus pulposus. Novel or existing nucleus replacements (NRs) may be added to the disc. The nucleus replacements may be made of natural or synthetic materials. Synthetic nucleus replacements may be made of, but are not limited to, polymers including polyurethane, silicon, hydrogels, or other elastomers.

One spinal repair system according to the invention comprises flexible longitudinal fixation components adapted for placement through portions of the AF with intact fibers, a porous mesh reinforcement component adapted for placement within or over a region of the AF with damaged fibers, and an optional anti-adhesion component for placement over flexible longitudinal fixation components and the porous mesh component. The invention also includes a targeting device that may be used to determine injured and uninjured areas of the AF that lie adjacent to a fissure or aperture in the AF.

Preferred embodiments of the invention include an intra-aperture component dimensioned for positioning within a defect in the AF, with one or more components being used to maintain the proper placement of the intra-aperture component. The intra-aperture component may be porous and flexible while being intentionally non-expandable in cross section following its positioning within the defect. A component used to maintain the intra-aperture component within the defect includes a flexible longitudinal fixation component that passes through the intra-aperture component and a region of the AF apart from the defect. If available, this may be a region of the AF having overlapping layers with intact fibers in different directions.

The flexible longitudinal fixation component may pass through a generally vertical passageway in the intra-aperture component and a region of the AF apart from the defect. The flexible longitudinal fixation component may be anchored to one of the upper and lower vertebral bodies. The components used to maintain the intra-aperture component within the defect includes a flexible longitudinal fixation component that passes twice through the intra-aperture component and is anchored to one of the upper and lower vertebral bodies. For example, the flexible longitudinal fixation component may form one or more loop or loops, each passing once through the AF and twice through the intra-aperture component.

Numerous instruments and tools are also disclosed, some in kit form along with implanted components, to orient the flexible longitudinal fixation components, place anchors, and so forth.

BRIEF DESCRIPTION OF THE DRAWINGS

FIG. 1A is a superior view of an unfolded intra-aperture component used in a preferred embodiment of the invention;

FIG. 1B is an oblique of the embodiment of the invention drawn in FIG. 1A;

FIG. 1C is a posterior view of an intervertebral disc (IVD) and the embodiment of the invention drawn in FIG. 1A;

FIG. 1D is a superior view of an axial cross section of an intervertebral disc (IVD) and the embodiment of the invention drawn in FIG. 1C;

FIG. 1E is an oblique view of an alternative embodiment of the invention drawn in FIG. 1A;

FIG. 1F is an oblique view of another alternative embodiment of the invention drawn in FIG. 1A;

FIG. 1G is an oblique view of another alternative embodiment of the invention drawn in FIG. 1A;

FIG. 1H is an oblique view of the transverse passageways that extend between or within the folds of the embodiment of the invention drawn in FIGS. 1A and 1C;

FIG. 4A is a superior view of an axial cross section of an IVD and a lateral view of the embodiment of the invention drawn in FIG. 3A;

FIG. 4B is a superior view of an axial cross section of an IVD and a lateral view of the embodiment of the invention drawn in FIG. 4A;

FIG. 4C is a superior view of an axial cross section of an IVD and a lateral view of the embodiment of the invention drawn in FIG. 4B;

FIG. 4D is a superior view of an axial cross section of an IVD and a lateral view of the embodiment of the invention drawn in FIG. 4C;

FIG. 11C is a lateral view of the distal end of a hook-like tool. The diameter of the tool is preferably slightly smaller than the diameter of the drill bit described in FIG. 11B;

FIG. 11D is a superior view of the distal end of the embodiment of the invention drawn in FIG. 11C;

FIG. 11E is a lateral view of the embodiments of the invention drawn in FIGS. 11B and 11C;

FIG. 11F is a lateral view of the embodiment of the invention drawn in FIG. 11E;

FIG. 11G is a lateral view of the embodiment of the invention drawn in FIG. 11F;

FIG. 15C is a view of the proximal end of a pedicle screw and the ends of flexible longitudinal fixation component drawn in FIG. 15A;

FIG. 15D is an exploded lateral view of the embodiment of the invention drawn in FIG. 15C;

FIG. 15E is lateral view of the embodiment of the invention drawn in FIG. 15D;

FIG. 17E is a view of the end of the component drawn in FIG. 17D;

FIG. 17F is a lateral view of the component drawn in FIG. 17D;

FIG. 17G is a posterior view of a spinal segment and the embodiments of the invention drawn in FIGS. 17A and 17D;

FIG. 17H is a lateral view of a partial sagittal cross section of a spinal segment and the embodiment of the invention drawn in FIG. 17G;

FIG. 17I is lateral view of an alternative embodiment of the invention drawn in FIG. 17H;

FIG. 17J is a view of the top of the embodiment of the invention drawn in FIG. 17I;

FIG. 17K is a view of the top of the embodiment of the invention drawn in FIG. 17J;

FIG. 22B is a lateral view of a partial sagittal cross section of three spinal laminae, the ligamentum flavum between the laminae, and the embodiment of the invention drawn in FIG. 22A;

FIG. 23A is a view of the top of an alternative embodiment of the invention drawn in FIG. 12A;

FIG. 23B is a posterior view of two spinous processes and the embodiment of the invention drawn in FIG. 23A;

FIG. 23C is a posterior view of the spinous processes and embodiment of the invention drawn in FIG. 23B;

FIG. 23D is a posterior view of a spinal segment and the embodiment of the invention drawn in FIG. 23C;

FIG. 24A is a posterior view of a portion of the spine and an alternative embodiment of the ingrowth sleeve drawn in FIG. 17D;

FIG. 24B is lateral view of a spinal segment and the embodiment of the invention drawn in FIG. 24A;

FIG. 24C is a view of a transverse cross section of a vertebra and the embodiment of the invention drawn in FIG. 24B FIG. 25A is an end view of an alternative embodiment of the inventions drawn in FIGS. 17E and 24B;

FIG. 25B is a lateral view of the embodiment of the invention drawn in FIG. 25A; and FIG. 25C is a posterior view of a spinal segment and the embodiment of the invention drawn in FIG. 25A.

DETAILED DESCRIPTION OF THE INVENTION

Figure 2A:
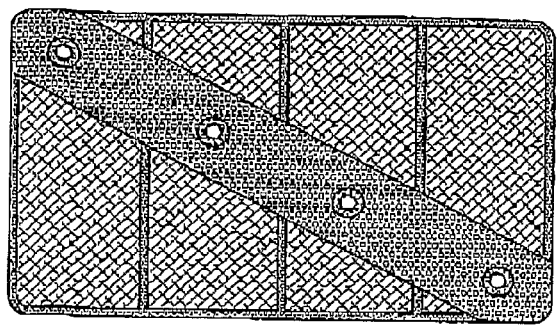
FIG. 2A is a superior view of an unfolded intra-aperture component used in the embodiment of the invention drawn in FIG. 2B.

FIG. 1A is a drawing of an intra-aperture component 100 constructed in accordance with the invention. In this and in other embodiments of the invention, the component is preferably made of synthetic mesh, allograft tissue or xenograft tissue. For example, the component could be made of polyester, polypropylene, or expanded polytetrafluoroethylene (ePTFE) mesh or allograft fascia. The intra-aperture component taught in this and other embodiments of the invention taught in this application is preferably 3 to 12 mm wide (left to right), tall (high), and long (proximal to distal). The intra-aperture component may be larger in alternative embodiments of the invention. The unfolded component shown in FIG. 1A is preferably 0.5 to 2.5 mm thick. For the purposes of this description, the intra-aperture component 100 has a proximal end 112 and a distal portion 108. Holes 104 may be provided near the distal end of the intra-aperture component 100, and the intra-aperture component may include a plurality of fold lines 106 running generally proximal-distal.

In the oblique representation of FIG. 1B, a flexible longitudinal fixation component 102 was passed through holes 104 in the intra-aperture component 100. The flexible longitudinal fixation component taught in this and other embodiments of the invention is preferably made of high tensile strength multi-filament or braided polyester. For example, the flexible longitudinal fixation component could be made of #2 to #5 sized Fiberwire (Arthrex, Naples, Fla., USA), Orthocord (DePuy Orthopaedics, Warsaw, Ind., USA), suture from Tornier (Edina, Minn., USA), nylon or other type or size suture material. The flexible longitudinal component is preferably 20 to 60 mm long.

The flexible longitudinal fixation component 102 generally passes through the intra-aperture component in a direction transverse to the proximal-distal orientation. The folds 106 and the direction that the flexible longitudinal fixation component passes through the intra-aperture component may be oriented in other directions in accordance with alternative embodiments of the invention.

The flexible longitudinal fixation component preferably passes through the reinforced area of the intra-aperture component several times. With four holes in the intra-aperture component of FIG. 1A, the component may be folded three times along the flexible longitudinal fixation component to create shape drawn in FIG. 1B. As discussed in more detail below, however, the flexible longitudinal fixation component may pass more or fewer times through the intra-aperture component in alternative embodiments of the invention.

The invention also maximizes the force required to tear the intra-aperture component, which would release the flexible longitudinal fixation component. In particular, the material which forms the distal portion 108 of the intra-aperture component is preferably reinforced to increase the tensile strength of the intra-aperture component in the area through which the flexible longitudinal fixation component passes. The material around the holes in intra-aperture component may be doubly reinforced (the additional circles surrounding the holes). Areas of reinforcement 109 are also seen around the edges of the component. For example, embroidery or other overstitching of bonding technology may be used to reinforce such areas.

FIG. 1C is a posterior view of an intervertebral disc (IVD) 110 and the embodiment of the invention drawn in FIG. 1A. The invention drawn in FIG. 1A was placed into an aperture or defective region 111 of the IVD. The ends of the flexible longitudinal fixation component 102 were welded over the proximal end of the intra-aperture component. The ends of the flexible longitudinal fixation component were passed through anulus fibrosis (AF) tissue on either side of the aperture before the ends were welded together.

As drawn in FIGS. 29M-29P, 30A-30B, and 36A-37F of U.S. patent application Ser. No. 12/263,753, the distal end of the flexible longitudinal fixation component was preferably passed through AF tissue on one side of the aperture, then through the holes in the intra-aperture component, then through AF tissue on the opposite side of the aperture, followed by tension on the ends of the flexible longitudinal fixation component before the ends of the flexible longitudinal component or otherwise fastened together.

The present invention facilitates nucleus pulposus (NP) tissue extrusion between AF tissue and the device and through or between the folds of the device. The spaces between folds of the device, which may be 2 to 11 mm or more tall, extend from the proximal to distal end of the intra-aperture component. Connective tissue preferably grows over the proximal end of the aperture, as occurs naturally, the first few days or weeks following surgery to prevent NP extrusion. Connective tissue also preferably grows into the aperture between the AF and the intra-aperture component and between the folds of the intra-aperture component days of weeks following surgery to prevent NP extrusion. Connective tissue also preferably grows through pores of the intra-aperture component and between the folds of the intra-aperture component a few days or weeks following surgery to prevent NP extrusion.

Naturally occurring connective tissue—not the implanted device—prevents NP tissue extrusion starting several days to weeks following surgery. The device does not seal the aperture per se. Rather, like a natural aperture in the AF, the device allows a limited amount of extrusion of NP tissue. Large NP pieces, too big to extrude, may be converted into smaller pieces of tissue that may extrude. Connective tissue grows over and into the treated aperture to eventually seal the aperture, however, thus preventing extrusion of the entire NP.

FIG. 1D is a superior view of an axial cross section of an intervertebral disc (IVD) and the embodiment of the invention drawn in FIG. 1C. The proximal end 112 of the intra-aperture component preferably sits flush with, or is recessed with respect to, the outer layer of the AF.

FIG. 1E is an oblique view of an alternative embodiment of the invention drawn in FIG. 1A. The intra-aperture component does not have folds. One, 2, 3, 4, 5, or more intra-aperture components per flexible longitudinal fixation components may be used in this and the other embodiments of the invention taught in this application. FIG. 1F is an oblique view of another alternative embodiment of the invention drawn in FIG. 1A. The intra-aperture component has a single fold.

FIG. 1G is an oblique view of another alternative embodiment of the invention drawn in FIG. 1A. The intra-aperture component has two folds. Four, five, six or more folds may be used in alternative embodiments of the invention. However, as drawn in FIGS. 1C and 1D, the folds are preferably oriented generally perpendicular to the lamellae of the AF so as to create intentional transverse passageways between the folds of the intra-aperture component. As discussed above, these passageways facilitate partial NP extrusion from the IVD before connective tissue in-growth across or into the aperture, thus preventing unwanted, excessive NP extrusion.

FIG. 1H is an oblique view of the transverse passageways that extend between or within the folds of the embodiment of the invention drawn in FIGS. 1A and 1C. The invention taught in this and other embodiments taught in this application and my co-pending U.S. patent application Ser. No. 12/263,753 create unobstructed transverse spaces or passageways that are preferably at least 2 mm tall or wide. Such unobstructed passageways extend from the proximal to the distal ends of the component to facilitate extrusion of NP tissue. The unobstructed passageways also extend from the NP to the exterior of the IVD. Such passageways are generally larger than 2 mm tall or wide and generally at least 3 mm long. For example, such passageways are generally 11 mm tall in 12 mm tall components with vertical folds and generally 11 mm wide in 12 mm wide components with horizontal folds. The transverse passageways between or within the folds are preferably 2, 3, 4, 5, 6, 7, 8, 9, 10, 11 mm wide or tall. Such passageways can be less than 2 or more than 11 mm wide or tall in alternative embodiments of the invention. The unobstructed passageways are preferably 3, 4, 5, 6, 7, 8, 9, 10, 11 mm long. Such passageways may be less than 3 or more than 11 mm long in alternative embodiments of the invention. Unobstructed spaces or passageways between the intra-aperture components and the apertures also facilitate NP extrusion through the aperture.

The folds of the intra-aperture component and the direction of the flexible longitudinal fixation component may be oriented in other directions in alternative embodiments of the invention. For example, FIG. 2A is a superior view of an unfolded intra-aperture component according to an alternative embodiment of the invention. The device is preferably made of the same materials and made in the same sizes as the device described in FIG. 1A. The folds of the device run generally proximal-distal. However, the holes are arranged diagonally, allowing the flexible longitudinal fixation component to pass through the intra-aperture component in a proximal-distal direction when the device is folded, as shown in FIG. 2B.

Figure 2B:
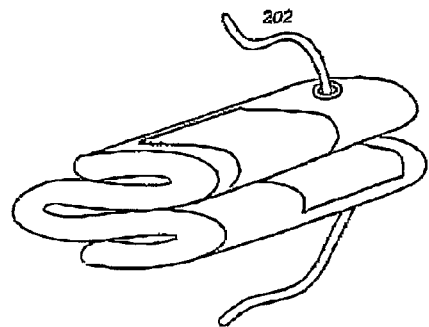
FIG. 2B is an oblique view of an alternative embodiment of the invention drawn in FIG. 1A.

The component is folded three times to create shape drawn in FIG. 2B. The intra-aperture component is preferably reinforced to increase the tensile strength of the intra-aperture component in the area through which the flexible longitudinal fixation component passes. The material around the holes in intra-aperture component is preferably doubly reinforced (additional circles surrounding the holes). Areas of reinforcement are also seen around the edges of the component. The unfolded component is preferably 0.5 to 2.5 mm thick. The invention maximizes the force required to pull tear the intra-aperture component thus releasing the flexible longitudinal fixation component.

The flexible longitudinal fixation component 202 passes through the reinforced area of the intra-aperture component four times. As drawn in FIGS. 2E-2F, the flexible longitudinal fixation component may pass through 1, 2, 3, or more holes in the intra-aperture component in alternative embodiments of the invention.

Figure 2C:
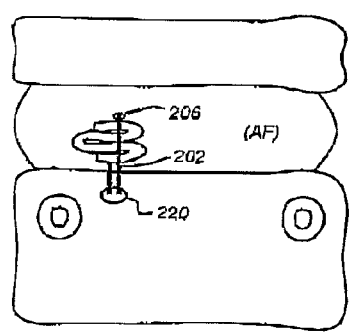
FIG. 2C is a posterior view of coronal cross section of a portion of the spine and the embodiment of the invention drawn in FIG. 2A.

FIG. 2C is a posterior view of a coronal cross section of a portion of the spine and the embodiment of the invention drawn in FIG. 2A. The invention drawn in FIG. 2A was placed into and aperture or defective region of the IVD. The ends of the flexible longitudinal fixation component 202 pass over the proximal end of the intra-aperture component and pass into a vertebral fixation component 220 as drawn in FIG. 48C of U.S. patent application Ser. No. 12/263,753.

The first end 206 of the flexible longitudinal fixation component was passed through anulus fibrosis (AF) tissue above the aperture, then through the holes in the intra-aperture component, then into the locking mechanism of the vertebral fixation component 220. The invention enables nucleus pulposus (NP) tissue to extrude between AF tissue and the device and through or between the folds of the device. The spaces between folds of the device are preferably 2 to 11 mm or more tall and extend from the proximal to distal end of the intra-aperture component. Connective tissue preferably grows over the proximal end of the aperture, as occurs naturally, the first few days of weeks following surgery to prevent NP extrusion. Connective tissue also preferably grows into the aperture between the AF and the intra-aperture component and between the folds of the intra-aperture component a few days or weeks following surgery to prevent NP extrusion. Connective tissue also preferably grows through pores of the intra-aperture component and between the folds of the intra-aperture component days of weeks following surgery to prevent NP extrusion. The device tightens during spinal flexion, the position most likely to expulse anulus repair devices, reducing the height of the aperture and thus reducing extrusion of NP tissue during spinal flexion.

Figure 2D:
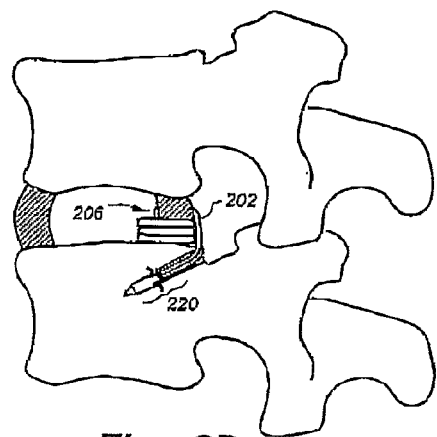
FIG. 2D is a lateral view of a partial sagittal cross section of a portion of the spine and the embodiment of the invention drawn in FIG. 2C.
Figure 2E:
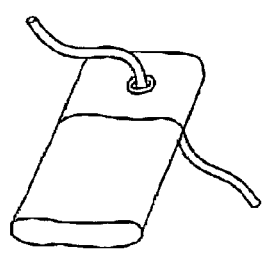
FIG. 2E is an oblique view of an alternative embodiment of the invention drawn in FIG. 2A.

FIG. 2D is a lateral view of a partial sagittal cross section of a portion of the spine and the embodiment of the invention drawn in FIG. 2C (and FIG. 48A of co-pending U.S. patent application Ser. No. 12/263,753), and FIG. 2E is an oblique view of an alternative embodiment of the invention drawn in FIG. 2A. The intra-aperture component does not have folds. One, 2, 3, 4, 5, 6, or more such components could be used per device in this and other embodiments of the invention taught in this application.

Figure 2F:
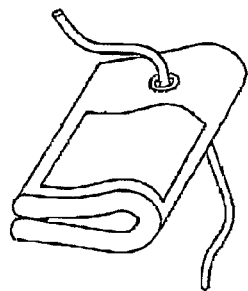
FIG. 2F is an oblique view of another alternative embodiment of the invention drawn in FIG. 1A.

FIG. 2F is an oblique view of another alternative embodiment of the invention drawn in FIG. 1A. The intra-aperture component has a single fold. Two, three, four, five, six or more folds may be used in alternative embodiments of the invention. However, as drawn in FIGS. 2C and 2D, the folds are preferably oriented generally perpendicular to the lamellae of the AF so as to create large transverse passageways between the folds of the intra-aperture component that facilitate NP extrusion from the IVD before connective tissue in-growth across of into the aperture prevents such NP extrusion. Such passageways preferably have surface areas of 16 to 288 or more mm squared and volumes of 16 to 576 or more mm cubed. Passageways with larger or smaller surface areas could be used in alternative embodiments of the invention.

Figure 3A:
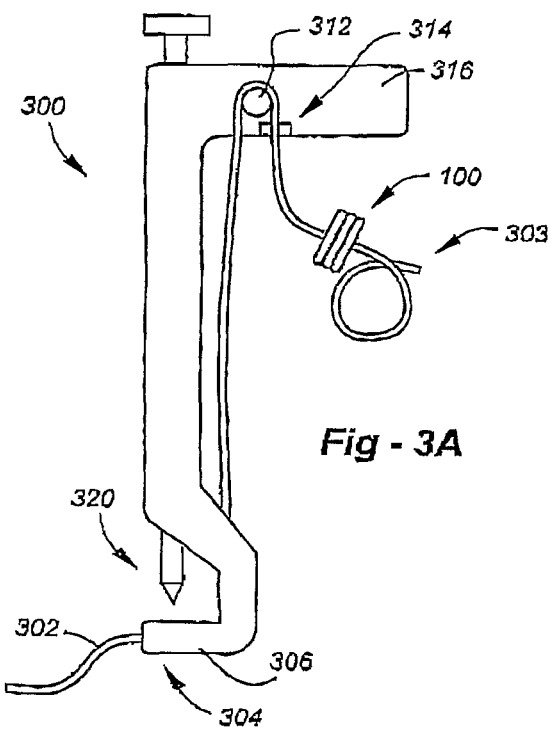
FIG. 3A is a lateral view of the embodiment of the invention drawn in FIG. 1A.

FIG. 3A is a lateral view of the embodiment of the invention drawn in FIG. 1A and a novel instrument 300 that may be used to pass the ends of the flexible longitudinal fixation component through the AF. The first end 302 of the flexible longitudinal fixation component is pressed into a releasable fastening feature at the tip 304 of the footplate 306 at the distal end of the tool. The first arm of the flexible longitudinal fixation component also passes through a slot like opening 310 on the bottom and posterior portions to the footplate of the instrument and wraps around a projection 312 on the handle 316 of the instrument 300. The first arm of the flexible longitudinal fixation component is then pressed into a releasable fastening feature 314 on the handle of the instrument.

The intra-aperture component 100 and the second arm 303 of the flexible longitudinal fixation component are seen hanging from the handle 316 of the instrument 300. The first arm of the flexible longitudinal fixation component is released with less force from the fastening component on the footplate of the instrument than the fastening component on the handle of the instrument. A needle-like component 320 passes through a cannulated shaft through the instrument. The tip of the needle preferably has a tapered point rather than a cutting point. A hook-like opening 322 is seen on the side of the needle component near the distal end of the component.

Figure 3B:
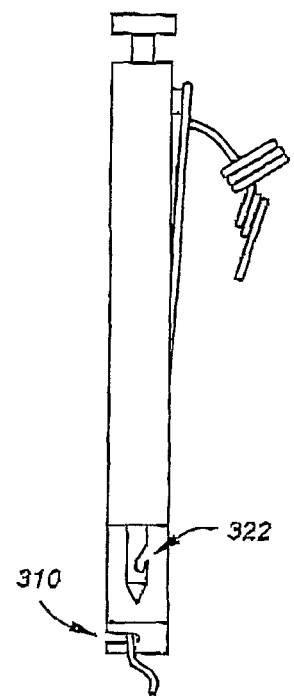
FIG. 3B is a lateral view of the embodiment of the invention drawn in FIG. 3A.

FIG. 3B is a lateral view of the embodiment of the invention drawn in FIG. 3A. The hook-like opening 322 is seen on the side of the distal end of the needle. The distal end of the first arm of the flexible longitudinal fixation component is seen in the releasable fastening feature at the end of the footplate of the instrument. For example, the flexible longitudinal fixation component may be press fit into a slot on the end of the footplate.

Figure 3C:
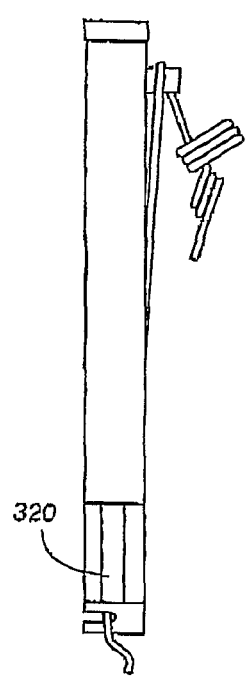
FIG. 3C is a lateral view of the embodiment of the invention drawn in FIG. 3B.

FIG. 3C is a lateral view of the embodiment of the invention drawn in FIG. 3B. The needle component 320 was advanced through the shaft of the tool. The needle component preferably has a feature that prevents axial rotation of the needle relative to the shaft of the tool. For example, the shaft of the tool may have a projection that cooperates with a slot in the side of the cannulated portion of the tool to prevent such axial rotation. The feature keeps the hook-like opening in the side of the needle parallel with the portion of the flexible longitudinal fixation component within the footplate portion of the instrument.

The needle component is preferably actuated by a compressible pistol grip mechanism in an alternative embodiment of the invention. Squeezing the pistol grip advances the needle component in the cannulated component in the alternative embodiment of the invention. The distal portion of the needle forces the flexible longitudinal fixation component to the side as the needle passes by the flexible longitudinal component. Tension on the flexible longitudinal fixation component causes the flexible longitudinal component to migrate into the hook-like opening in the needle-like component of the tool.

Figure 3D:
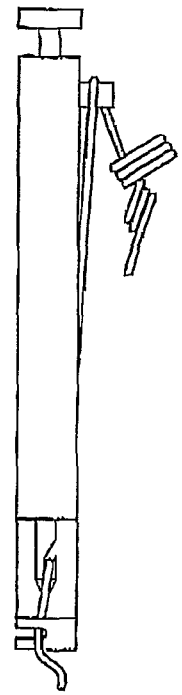
FIG. 3D is lateral view of the embodiment of the invention drawn in FIG. 3C.

FIG. 3D is lateral view of the embodiment of the invention drawn in FIG. 3C with the needle partially retracted. The distal portion of the first end of the flexible longitudinal fixation component was captured in the hook-like opening in the side of the needle. Retraction of the needle pulls the distal end of the flexible longitudinal fixation component through the releasable fastening feature at the end of the footplate. The stronger releasable fastening feature on the handle of the instrument preferably prevents advancement of the proximal portion of the first arm of the flexible longitudinal fixation component as the needle is retracted.

Figure 3E:
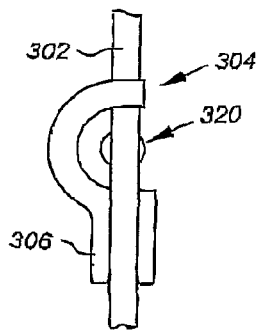
FIG. 3E is view of the bottom of the footplate of the embodiment of the invention drawn in FIG. 3C.

FIG. 3E is view of the bottom of the footplate of the embodiment of the invention drawn in FIG. 3C. The distal portion of the first arm of the flexible longitudinal fixation component is seen within the slot in the bottom of the footplate and in the releasable fastening feature in the footplate.

Figure 3F:
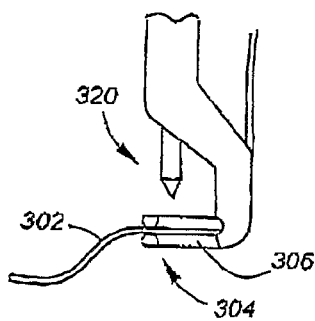
FIG. 3F is the opposite lateral view of the distal portion of the embodiment of the invention drawn in FIG. 3A.

FIG. 3F is the opposite lateral view of the distal portion of the embodiment of the invention drawn in FIG. 3A. The hook-like opening is on the opposite side of the needle. The taper point of the needle slides by the flexible longitudinal fixation component as the needle is advanced through the cannula of the instrument. The instrument is preferably manufactured in various sizes. For example, instruments with 3 mm, 6 mm and 9 mm long footplates could be manufactured. The space between the footplate and the distal portion of the cannula portion of the instrument, where the tip of the needle component exits, is preferably 5 to 25 mm long or longer.

Figure 3G:
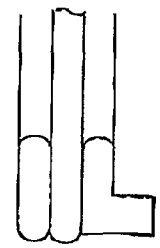
FIG. 3G is a posterior view of the distal portion of the embodiment of the invention drawn in FIG. 3A.

FIG. 3G is a posterior view of the distal portion of the embodiment of the invention drawn in FIG. 3A. The distal portion of the first arm of the flexible longitudinal fixation component is seen in a slot-like opening in the back of the tool. Tension on the first arm of the flexible longitudinal fixation component holds the first arm of the flexible longitudinal fixation component in the slot-like openings of the instrument. Tension on such component is achieved by fastening the distal end of the first arm of the flexible longitudinal fixation component in the releasable fastening feature at the top of the footplate and pulling in the proximal portion of the first arm of the flexible longitudinal fixation component as such component is wrapped around the projection from the handle and temporarily locked into the releasable fastening component.

Figure 3H:
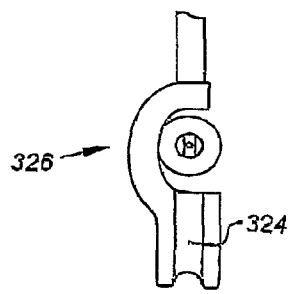
FIG. 3H is a view of the bottom of an alternative embodiment of the invention drawn in FIG. 3A.

FIG. 3H is a bottom view of an alternative embodiment of the invention drawn in FIG. 3A. The flexible longitudinal fixation component was not included in the drawing to better illustrate the bottom of the instrument. The groove 324 in the footplate 326 that receives the distal portion of the first arm of the flexible longitudinal fixation component is seen on the bottom of the tool.

Figure 3I:
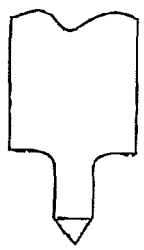
FIG. 3I is a lateral view of the distal end of the needle of the embodiment of the invention drawn in FIG. 3H.
Figure 3J:
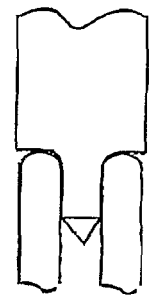
FIG. 3J is a lateral view of the embodiment of the invention drawn in FIG. 3I and a portion of a flexible longitudinal fixation component.

FIG. 3I is a lateral view of the distal end of the needle of the embodiment of the invention drawn in FIG. 3H. FIG. 3J is a lateral view of the embodiment of the invention drawn in FIG. 3I and a portion of a flexible longitudinal fixation component. The sides of the distal portion of the needle preferably have recesses that provide space for the flexible longitudinal fixation component. The hook-like feature in the needle is on the opposite side of the drawing, and not visible in this view.

Figure 3K:
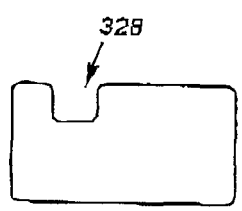
FIG. 3K is lateral view of an alternative footplate of the embodiment of the invention drawn in FIG. 3A.
Figure 3L:
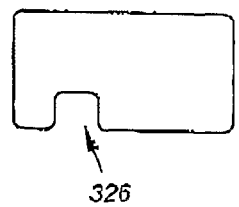
FIG. 3L is a lateral view of an alternative embodiment of the footplate drawn in FIG. 3A.

FIG. 3K is lateral view of an alternative footplate of the embodiment of the invention drawn in FIG. 3A. A slot-like releasable fastening feature 328 is on the top of the distal end of the footplate. FIG. 3L is a lateral view of an alternative embodiment of the footplate drawn in FIG. 3K. The slot-like releasable fastening feature 329 is on the bottom of the distal end of the footplate. The slot-like releasable fastening feature or other releasable fastening feature could be located in other areas of the tool in alternative embodiments of the invention.

Figure 3M:
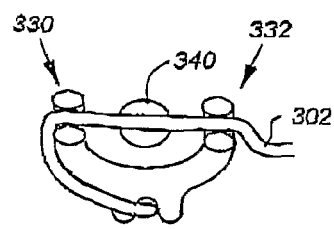
FIG. 3M is a view of the bottom of an alternative embodiment of the invention drawn in FIG. 3E.

FIG. 3M is a view of the bottom of an alternative embodiment of the invention drawn in FIG. 3E. Two releasable fastening features 330, 332 hold the distal end of the first arm of the flexible longitudinal fixation component 302. The captured distal portion of the first arm of the flexible longitudinal fixation component generally takes a transverse course relative the handle of the instrument and is generally perpendicular to such portion of the flexible longitudinal fixation component drawn in FIG. 3E.

Figure 3N:
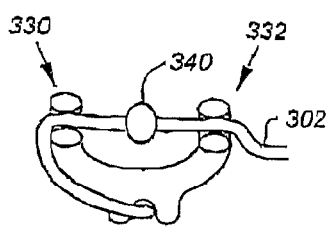
FIG. 3N is a view of the bottom of the embodiment of the invention drawn in FIG. 3M.
Figure 3O:
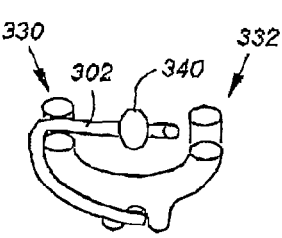
FIG. 3O is a view of the bottom of the embodiment of the invention drawn in FIG. 3N.

FIG. 3N is a view of the bottom of the embodiment of the invention drawn in FIG. 3M. The tip of the needle 340 was advanced by the captured portion of the flexible longitudinal fixation component. The segment of the captured portion of the flexible longitudinal sits within the hook-like opening on the side of the needle component. FIG. 3O is a view of the bottom of the embodiment of the invention drawn in FIG. 3N. The needle 340 was partially retracted into the shaft of the instrument. Such movement of the needle pulled the distal end of the first arm of the flexible longitudinal fixation component from the releasable fastening feature 332.

FIG. 4A is a superior view of an axial cross section of an IVD and a lateral view of the embodiment of the invention drawn in FIG. 3A. The footplate 306 of the invention drawn in FIG. 3A was placed through an aperture 402 in the IVD, generally rotated 90 degrees and pressed against the inner portion of the AF. FIG. 4B is a superior view of an axial cross section of an IVD and a lateral view of the embodiment of the invention drawn in FIG. 4A. The tip 320' of needle 320 of the instrument was advanced the AF and by the distal portion of the first arm of the flexible longitudinal fixation component 302. The taper tip of the needle preferably separates rather cuts the fibers of the AF. Tension on the first arm of the flexible longitudinal fixation component causes the component to slip into the hook-like opening in the side of the needle.

FIG. 4C is a superior view of an axial cross section of an IVD and a lateral view of the embodiment of the invention drawn in FIG. 4B. The needle 302 of the instrument was withdrawn from the IVD which pulls the distal portion of the first arm of the flexible longitudinal fixation component 302 through the opening the AF created by the needle. The distal portion of the first arm of the flexible longitudinal fixation component advanced partially through the releasable fastening feature in the footplate.

FIG. 4D is a superior view of an axial cross section of an IVD and a lateral view of the embodiment of the invention drawn in FIG. 4C. The needle of the instrument was retracted further along the shaft of the instrument. The distal portion of the first arm of the flexible longitudinal fixation component was pulled through the releasable fastening feature in the footplate.

Figure 4E:
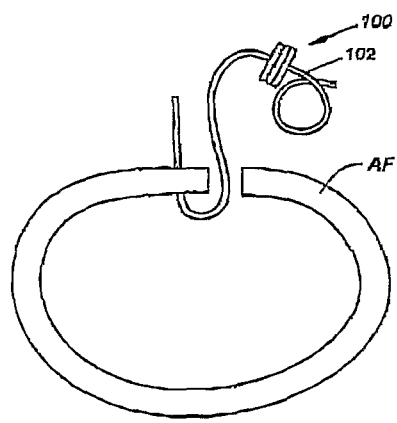
FIG. 4E is a superior view of an axial cross section of an IVD and a lateral view of the embodiment of the invention drawn in FIG. 4D.

FIG. 4E is a superior view of an axial cross section of an IVD and a lateral view of the embodiment of the invention drawn in FIG. 4D. The device 100 drawn in FIG. 1B was released from the instrument and the instrument drawn in FIG. 3A was removed from IVD. The ends of the arms of the flexible longitudinal fixation component 102 could be passed through vertebral fixation component as described in FIG. 29Q of my co-pending U.S. patent application Ser. No. 12/263,753.

Figure 4F:
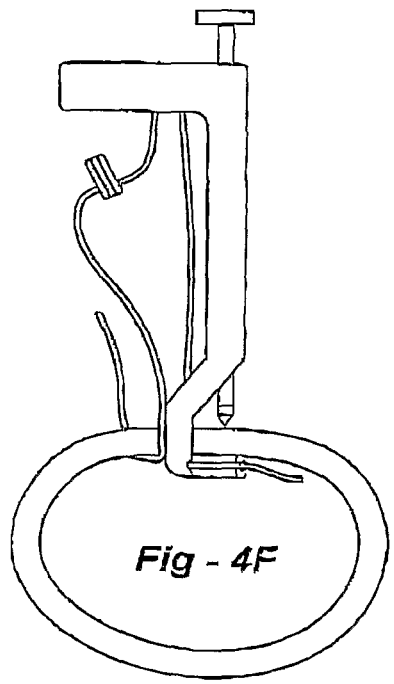
FIG. 4F is a superior view of an axial cross section of an IVD and a lateral view of the embodiment of the invention drawn in FIG. 4C.
Figure 4G:
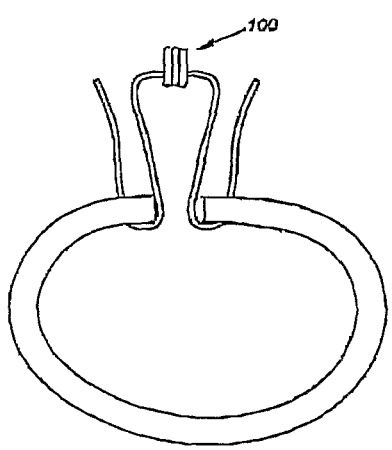
FIG. 4G is a superior view of an axial cross section of an IVD and a lateral view of the embodiment of the invention drawn in FIG. 4F.

FIG. 4F is a superior view of an axial cross section of an IVD and a lateral view of the embodiment of the invention drawn in FIG. 4C. The second arm of the flexible longitudinal fixation component was loaded into the instrument as described in the text of FIGS. 3A-4E. FIG. 4G is a superior view of an axial cross section of an IVD and a lateral view of the embodiment of the invention drawn in FIG. 4F. The second arm of the flexible longitudinal fixation component was passed through the AF as described in the text of FIGS. 3A-4F and the instrument was removed from the IVD.

Figure 4I:
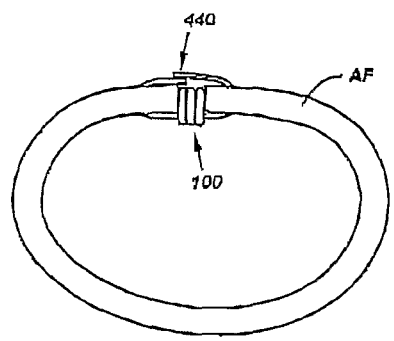
FIG. 4I is a superior view of an axial cross section of the IVD and the embodiment of the invention drawn in FIG. 4H.
Figure 4H:
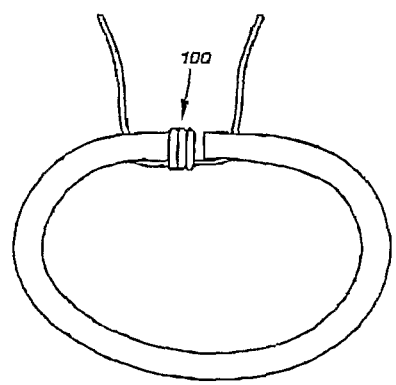
FIG. 4H is a superior view of an axial cross section of the IVD and the embodiment of the invention drawn in FIG. 4G.

FIG. 4H is a superior view of an axial cross section of the IVD and the embodiment of the invention drawn in FIG. 4G. The intra-aperture component was pulled into the aperture of the IVD by pulling on the ends of the arms of the flexible longitudinal fixation component. Intra-aperture components used in the inventions taught in this and my co-pending application U.S. patent application Ser. No. 12/263,753 are narrower than the widths of the apertures in the AF or shorter than the heights of the apertures or both narrower or shorter than the apertures. The cross sectional areas of the intra-aperture components including pores in the material used to manufacture the components are preferably 5 to 25 percent smaller than the cross sectional areas of the apertures to be treated.

Alternatively, the cross sectional areas of the intra-aperture components including pores in the material can be 1, 2, 3, 4, 26, 27, 28, less than 1, or more than 28 percent smaller than the cross sectional areas of the apertures to be treated. That is, the intra-aperture components leave 5 to 25 percent of the cross sectional areas of the apertures unfilled. Alternatively, the intra-aperture components leave 1, 2, 3, 4, 26, 27, 28, less than 1, or more than 28 percent of the cross sectional areas of the apertures unfilled. Preferably no dimension of the intra-aperture components, other than length, is larger than the corresponding dimension of the apertures to be treated.

The intra-aperture components preferably do not dilate the apertures in any direction. Alternatively, intra-aperture components could be larger than the apertures to be treated in one or more direction as long as such components are smaller than such apertures in on or more alternative directions so as to facilitate NP extrusion around the device in alternative embodiments of the invention. Alternatively, the outer portion the device could dilate the aperture so long as the transverse passageways remain open and allow NP tissue extrusion in alternative embodiments of the invention.

FIG. 4I is a superior view of an axial cross section of the IVD and the embodiment of the invention drawn in FIG. 4H. Tension on the ends of the arms of the flexible longitudinal fixation component preferably decreases the width of the aperture from the inlet to the outlet of the aperture in the AF. The arms of the flexible longitudinal fixation component were welded at 440 while tension was maintained on the arms of the flexible longitudinal component.

The invention taught in this embodiment and other embodiments of the invention taught in this application and my co-pending U.S. patent application Ser. No. 12/263,753 narrow apertures by tension on the flexible longitudinal fixation components and use of intra-aperture components that are substantially more narrow or shorter than the apertures in the AF. Tension on the arm or arms of the flexible longitudinal fixation component that passes across the aperture at or near the inlet narrows the inlet of the aperture and tension on the arm or arms of the flexible longitudinal fixation that passes across the aperture at or near the outlet narrows the outlet of the aperture. The central portion of the aperture is narrowed by tension on the portions of the flexible longitudinal fixation components that lie adjacent to the central portion of the aperture. Intra-aperture components used in this invention preferably do not swell or expand in situ and thus do not enlarge the aperture in the AF following insertion of the device into the spine.

Figure 4J:
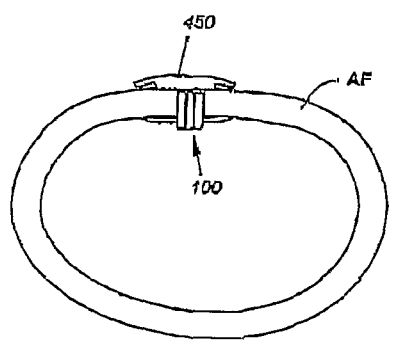
FIG. 4J is a superior view of an axial cross section of the IVD and the embodiment of the invention drawn in FIG. 4I.

FIG. 4J is a superior view of an axial cross section of the IVD and the embodiment of the invention drawn in FIG. 4I. An anti-adhesion sleeve 450 as described in FIGS. 38A-39B of my co-pending U.S. patent application Ser. No. 12/263,753 was applied over the arms of the flexible longitudinal fixation component before the flexible longitudinal components were welded.

Figure 5A:
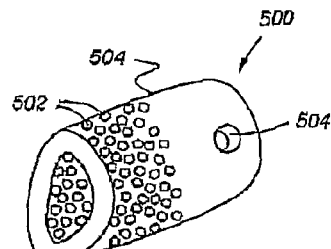
FIG. 5A is an oblique view of an alternative embodiment of the invention drawn in FIG. 1F.

FIG. 5A is an oblique view of an alternative embodiment of the invention drawn in FIG. 1F. Pores 502 extend through the proximal portion of a tube-like component 500. A pair of transverse holes 504 extend through the distal portion of the component 500. The device is preferably composed of ePTFE, and supplied in sizes described in the text of FIG. 1A. The device could be made of the other materials listed in the text of FIG. 1A in alternative embodiments of the invention. The pores in the proximal portion of the device are preferably 0.001 to 2.0 mm in diameter. The pores may be circular, square, rectangular, diamond, or other shape.

Figure 5B:
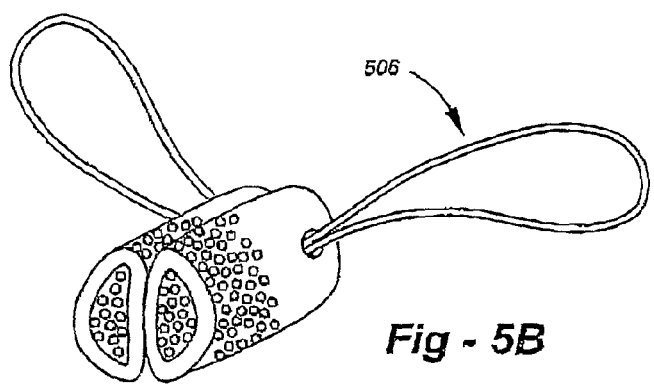
FIG. 5B is an oblique view of an alternative embodiment of the invention drawn in FIG. 5A.

FIG. 5B is an oblique view of an alternative embodiment of the invention drawn in FIG. 5A. A flexible longitudinal fixation hoop 506 was inserted through two of the components drawn in FIG. 5A. The flexible longitudinal fixation component is made of the materials and lengths described in the text of FIG. 1A and other portions of this application. One, 3, 4, 5, 6, or more intra-apertures per flexible longitudinal component could be used in alternative embodiments of the invention.

Figure 6A:
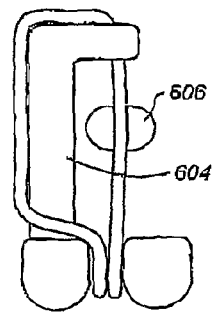
FIG. 6A is view of the bottom of an alternative embodiment of the invention drawn in FIG. 3E.

FIG. 6A is view of the bottom of an alternative embodiment of the invention drawn in FIG. 3E. The distal portion of first loop-like arm of the flexible longitudinal fixation component drawn in FIG. 5B is releasably fastened to the footplate 604 of the instrument. A portion of the loop is held in a slot-like releasable fastening feature in the side of the distal end of the footplate similar to the configuration drawn in FIG. 3F. The proximal portion of the first loop-like arm of the flexible longitudinal fixation component extends along the back of the instrument similar to the configuration drawn in FIG. 3F. The device drawn in FIG. 5B is temporarily fastened, under tension, to the handle of an instrument similar to the handle drawn in FIG. 3A.

Figure 6B:
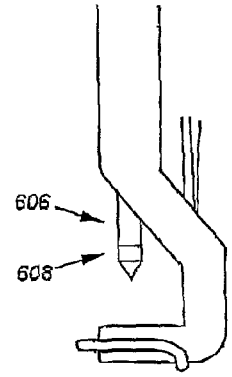
FIG. 6B is a lateral view of the distal portion of the embodiment of the invention drawn in FIG. 6A.

FIG. 6B is a lateral view of the distal portion of the embodiment of the invention drawn in FIG. 6A. The needle component 606 with a hook-like opening 608 in the side of the needle is seen above the distal portion of the first loop-like arm of the flexible longitudinal fixation component drawn in FIG. 5B.

Figure 6C:
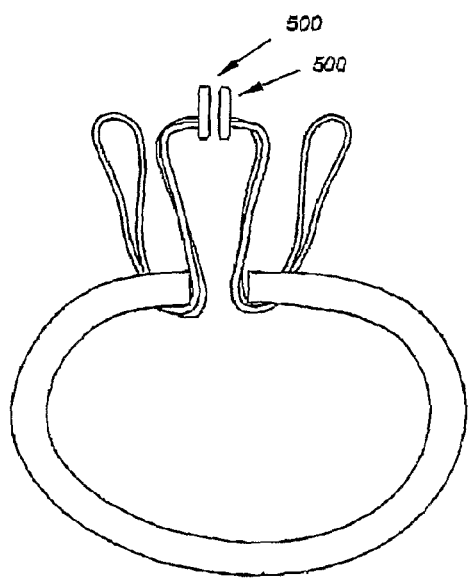
FIG. 6C is a superior view of a transverse cross section of an IVD and the embodiment of the invention drawn in FIG. 5B.

FIG. 6C is a superior view of a transverse cross section of an IVD and the embodiment of the invention drawn in FIG. 5B. The instrument drawn in FIGS. 6A and 6B was used to pull the distal portions of the loop-like arms of the flexible longitudinal fixation component through AF tissue on either side of the aperture. The tool works similar to the tool drawn in FIG. 3A-O, but pulls a flexible longitudinal fixation loop, rather than the end of a flexible longitudinal fixation component through the AF. Alternatively, the instrument may be used to create a loop shape of a flexible longitudinal fixation component by pulling a segment of the distal portion of a flexible longitudinal fixation component through the AF, but not pulling the distal end of the flexible longitudinal fixation component through the AF. The second loop-like arms of the flexible longitudinal fixation component are released from the fastening feature on the handle of the instrument as the needle is retracted into the shaft of the instrument. Tension on the two loop-like arms of the flexible longitudinal fixation component pulls the intra-aperture component into the aperture in the AF.

Figure 6D:
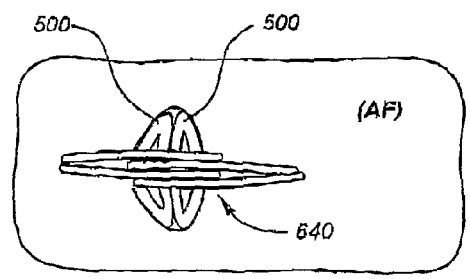
FIG. 6D is a posterior view of an IVD and the embodiment of the invention drawn in FIG. 6C.

FIG. 6D is a posterior view of an IVD and the embodiment of the invention drawn in FIG. 6C. The proximal ends of the intra-aperture components drawn in FIG. 5B are seen in the aperture in the AF. The ends of the loop-like flexible longitudinal fixation component were cut and removed leaving two separate flexible longitudinal fixation components that pass through AF tissue on either side of the aperture and through the intra-aperture components. If the loop-like flexible longitudinal fixation component has a weak area, for example an area where two ends of a single flexible longitudinal fixation component were welded to create the loop shown in FIG. 5B, the weakened area should be included in one of the two portions of the loop removed to create two separate longitudinal components.

The ends of the flexible longitudinal fixation components were welded or otherwise fastened at 640 after placing tension on the flexible longitudinal fixation components. An anti-adhesion sleeve, such as drawn in FIGS. 38E and 40B of my co-pending U.S. patent application Ser. No. 12/263,753 could have been threaded over the ends of the flexible longitudinal fixation component before welding such flexible longitudinal components in alternative embodiments of the invention.

Figure 7A:
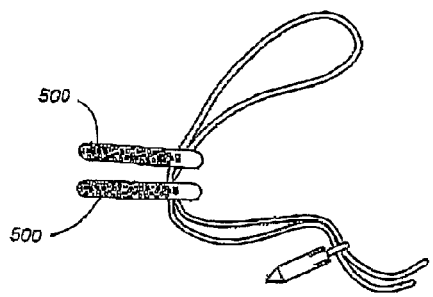
FIG. 7A is a lateral view of an alternative embodiment of the invention drawn in FIG. 5B.

FIG. 7A is a lateral view of an alternative embodiment of the invention drawn in FIG. 5B. The flexible longitudinal fixation component passes through two intra-aperture components 500 drawn in FIG. 5A. One, 3, 4, 5, 6, or more intra-aperture components per flexible longitudinal fixation component could be used in alternative embodiments of the invention. The ends of the flexible longitudinal fixation component were passed through vertebral fixation member 720. Co-pending application U.S. Ser. No. 12/263,753 describes suitable vertebral fixation members, intra-aperture components, and flexible longitudinal fixation component for this embodiment of the invention and other embodiments taught in this application.

Figure 7B:
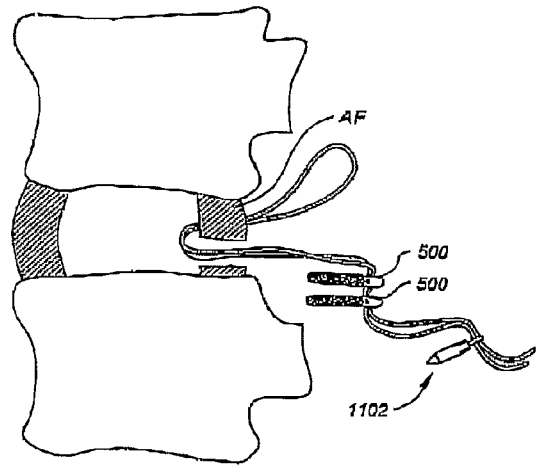
FIG. 7B is a lateral view of a partial sagittal cross section of a spinal segment and the embodiment of the invention drawn in FIG. 7A.

FIG. 7B is a lateral view of a partial sagittal cross section of a spinal segment and the embodiment of the invention drawn in FIG. 7A. The loop-like arm of the flexible longitudinal fixation component was passed through AF tissue cranial to the aperture using the instrument taught in FIGS. 6A and 6B.

Figure 7C:
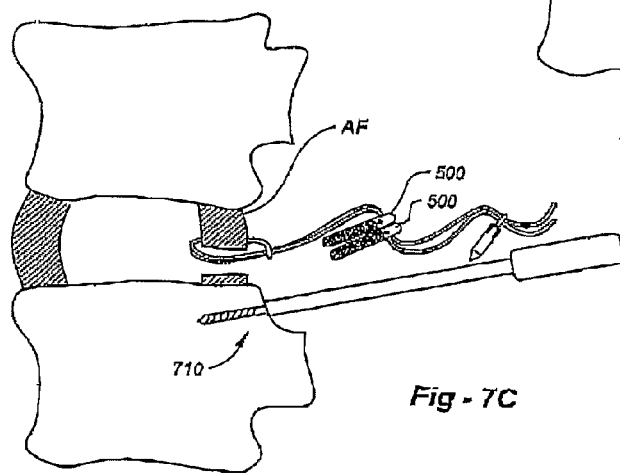
FIG. 7C is a lateral view of a partial sagittal cross section of the spinal segment and the embodiment of the invention drawn in FIG. 7B.

FIG. 7C is a lateral view of a partial sagittal cross section of the spinal segment and the embodiment of the invention drawn in FIG. 7B. The vertebral fixation component 720, intra-aperture components 500 and most of the flexible longitudinal fixation component were passed through the loop in the first arm of the flexible longitudinal component. A drill 710 was placed into the caudal vertebra. The position of the drill bit may be verified with x-ray or fluoroscopy.

Figure 7D:
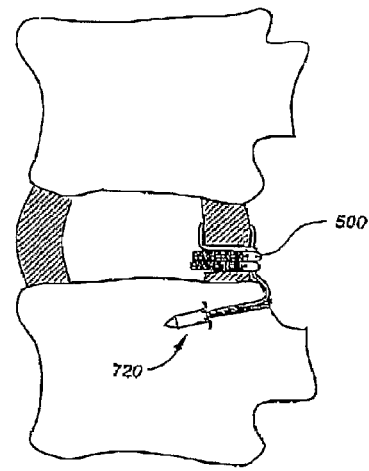
FIG. 7D is a lateral view of a partial sagittal cross section of the spinal segment and the embodiment of the invention drawn in FIG. 7C.

FIG. 7D is a lateral view of a partial sagittal cross section of the spinal segment and the embodiment of the invention drawn in FIG. 7D. The vertebral fixation component 720 was inserted, preferably by impaction, into the vertebra. A knot-pusher surgical instrument (not shown) could be used to tighten the flexible longitudinal fixation component before inserting the intra-aperture components 500 into the aperture and the vertebral fixation component into the vertebra. Tension on the ends of the flexible longitudinal fixation components provides the final tightening of the construct. The vertebral fixation member preferably has a cinch-like mechanism to permit tightening and locking of the arms of the flexible longitudinal fixation component.

Figure 7E:
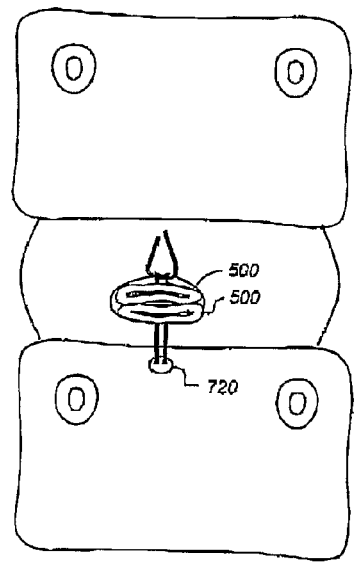
FIG. 7E is a posterior view of a coronal cross section of the spinal segment and the embodiment of the invention drawn in FIG. 7D.

FIG. 7E is a posterior view of a coronal cross section of the spinal segment and the embodiment of the invention drawn in FIG. 7D. The device tightens during spinal flexion, the position most likely to expulse anulus repair devices and NP tissue.

Figure 8A:
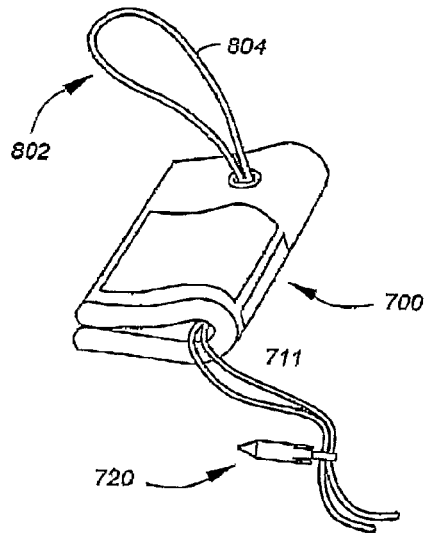
FIG. 8A is an oblique view of an alternative embodiment of the inventions drawn in FIGS. 2F and 7A

FIG. 8A is an oblique view of an alternative embodiment of the inventions drawn in FIGS. 2F and 7A. The loop-like end 802 of the flexible longitudinal fixation component 804 extends through a hole in the superior portion of the intra-aperture component 700. The ends of the flexible longitudinal fixation component were passed through a vertebral fixation component 720 as described in the text of FIG. 7A. Portions of the flexible longitudinal fixation component also pass through a fold 711 in the intra-aperture component 700. Alternative intra-aperture components, such as those drawn in FIGS. 1A-7A, could be used in this embodiment of the invention, the embodiment of the invention drawn in FIG. 5B, 7A and other embodiments of the invention.

Figure 8B:
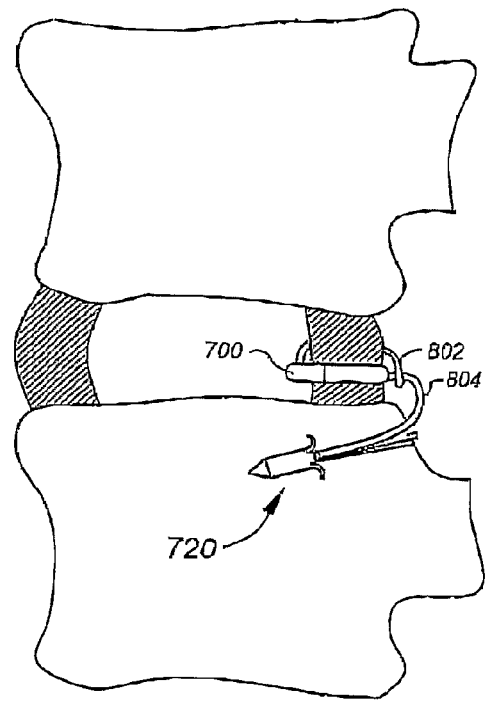
FIG. 8B is a lateral view of a coronal cross section of a spinal segment and the embodiment of the invention drawn in FIG. 8A.

FIG. 8B is a lateral view of a coronal cross section of a spinal segment and the embodiment of the invention drawn in FIG. 8A. The device 700 was inserted into the spine using the method taught in FIG. 7B-D. Tension is applied to the ends of the flexible longitudinal fixation component in the next step of the method.

Figure 8C:
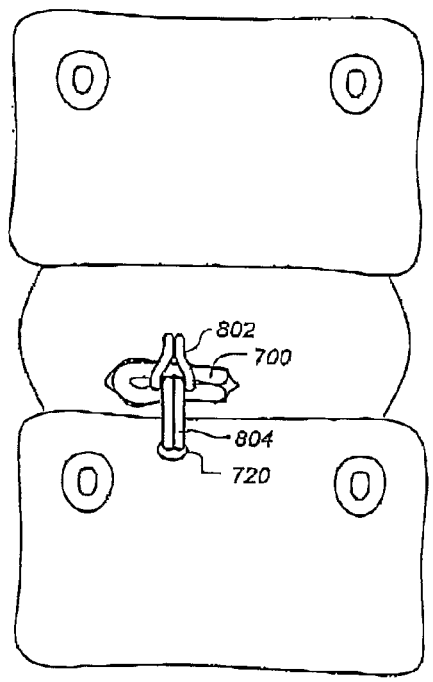
FIG. 8C is posterior view of a coronal cross section of the spinal segment and the embodiment of the invention drawn in FIG. 8B.

FIG. 8C is posterior view of a coronal cross section of the spinal segment and the embodiment of the invention drawn in FIG. 8B. The invention was used to treat a transverse aperture in the AF near a vertebra. Vertebral fixation components may be placed into the vertebrae caudal or cranial to the defective IVD in this embodiment of the invention and other embodiments taught in this application.

Figure 8D:
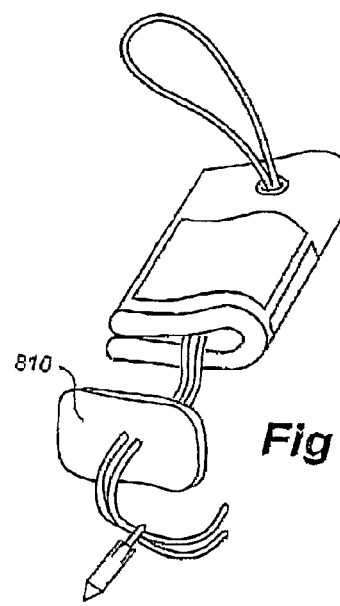
FIG. 8D is an oblique view of an alternative embodiment of the invention drawn in FIG. 8A.

FIG. 8D is an oblique view of an alternative embodiment of the invention drawn in FIG. 8A. The ends of the flexible longitudinal fixation component were threaded through holes in an anti-adhesion patch 810 before they were passed through the vertebral fixation component.

Figure 8E:
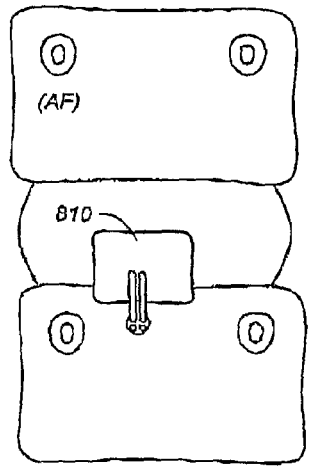
FIG. 8E is a posterior view of a coronal cross section of a spinal segment and the embodiment of the invention drawn in FIG. 8D.

FIG. 8E is a posterior view of a coronal cross section of a spinal segment and the embodiment of the invention drawn in FIG. 8D. The device was inserted into the spine using the method taught in FIGS. 8B and 8C. The anti-adhesion component is preferably made of ePTFE or other material described in this and my co-pending my co-pending application U.S. patent application Ser. No. 12/263,753. The patch component covers the intra-aperture component, the aperture in the AF, and the loop-like portion of the flexible longitudinal fixation component.

Figure 8F:
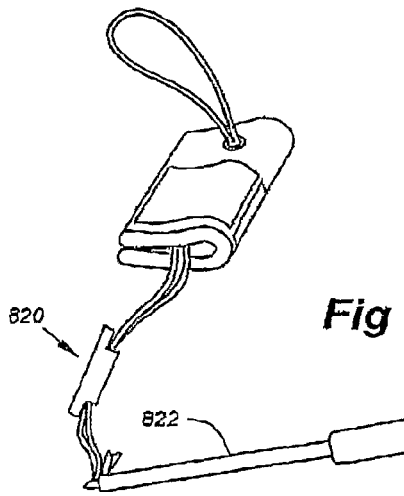
FIG. 8F is an oblique view of an alternative embodiment of the invention drawn in FIG. 8D.

FIG. 8F is an oblique view of an alternative embodiment of the invention drawn in FIG. 8D. The ends of the flexible longitudinal fixation component were threaded through holes in an anti-adhesion component 820 before they were passed through the vertebral fixation component. The anti-adhesion component was previously described FIG. 39A of my co-pending application U.S. patent application Ser. No. 12/263, 753. The vertebral fixation component extends from the shaft of an insertion instrument 822. The fully assembled or pre-coupled device is applied to the spine using the method taught in FIGS. 7A to 7D. The loop of the flexible longitudinal fixation component is pulled through the anulus using the tool described in FIGS. 6A and 6B. Then insertion instrument 822, the anchor extending from the insertion instrument and ends of the flexible longitudinal fixation component, which pass through the anchor, and the anti-adhesion component are passed through the loop of the flexible longitudinal fixation component. The mesh component is placed into the aperture in the anulus and the anchor is impacted into the vertebra in the next step of the procedure. Fully pre-coupled devices taught in this and other embodiments of the invention do not require intra-operative assembly by surgeons. The invention saves surgeons time and eliminates the risk of improperly coupling components during surgical procedures.

Figure 8G:
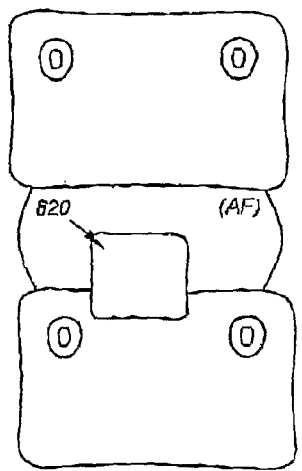
FIG. 8G is a posterior view of a coronal cross section of a spinal segment and the embodiment of the invention drawn in FIG. 8F.

FIG. 8G is a posterior view of a coronal cross section of a spinal segment and the embodiment of the invention drawn in FIG. 8F. The device was inserted into the spine using the method taught in FIGS. 8B and 8C. The anti-adhesion component is preferably made of ePTFE or other material described in this or my other pending applications. The patch component 820 covers the intra-aperture component, the aperture in the AF, and the flexible longitudinal fixation component, and the hole in the vertebra through which the vertebral fixation component was inserted.

Figure 9A:
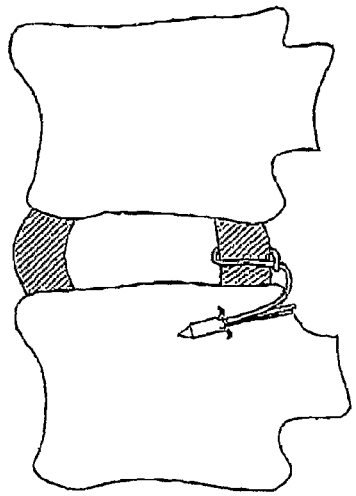
FIG. 9A is a lateral view of a partial sagittal cross section of a spinal segment and an alternative embodiment of the invention drawn in FIG. 8A.

FIG. 9A is a lateral view of a partial sagittal cross section of a spinal segment and an alternative embodiment if the invention drawn in FIG. 8A. The device does not have an intra-aperture component. The flexible longitudinal fixation and vertebral fixation components were inserted into the spine using the method taught in FIGS. 8B and 8C. Portions of the flexible longitudinal fixation component pass through the aperture in the IVD.

Figure 9B:
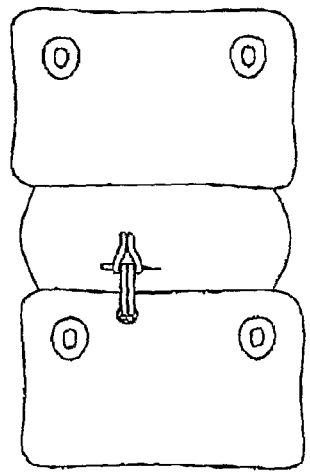
FIG. 9B is a posterior view of a partial coronal cross section of the spinal segment and the embodiment of the invention drawn in FIG. 9A.

FIG. 9B is a posterior view of a partial coronal cross section of the spinal segment and the embodiment of the invention drawn in FIG. 9B. The anti-adhesion patch component drawn in FIG. 8D could be added to alternative embodiments of the invention.

Figure 10A:
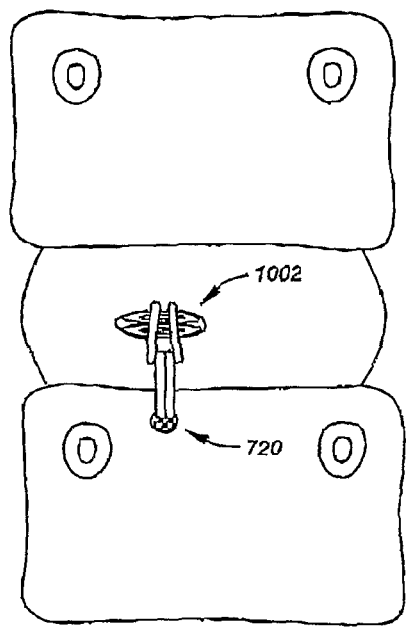
FIG. 10A is a posterior view of a partial coronal cross section of a spinal segment and an alternative embodiment of the inventions drawn in FIGS. 6C and 8C.

FIG. 10A is a posterior view of a partial coronal cross section of a spinal segment and an alternative embodiment of the inventions drawn in FIGS. 6C and 8C. The first loop-like arm of the flexible longitudinal fixation component was passed through AF tissue cranial to the aperture and the second loop-like arm was passed through AF tissue caudal to the aperture using the method taught in FIGS. 8B and 8C. The second loop-like are of the flexible longitudinal fixation component was passed through the first loop-like arm of the component.

The end of the second loop-like arm of the flexible longitudinal fixation component was cut and removed leaving two ends that were threaded through a vertebral fixation component 720. As described in the text of FIG. 6D, if the loop-like flexible longitudinal fixation component has a weak area, for example an area where two ends of a single flexible longitudinal fixation component were welded to create the loop, the weakened area should be included in the portion of the loop removed to create two ends of the longitudinal component. The vertebral fixation component was impacted into the caudal vertebra. Two intra-aperture components 1002 are seen within a horizontal aperture in the AF.

Figure 10B:
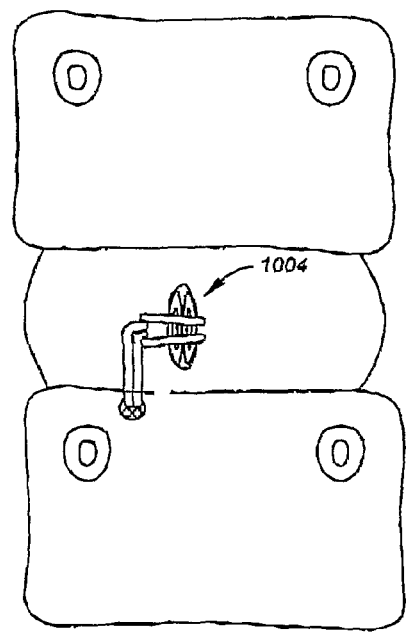
FIG. 10B is a posterior view of a partial coronal cross section of a spinal segment and the embodiment of the invention drawn in FIG. 10A.

FIG. 10B is a posterior view of a partial coronal cross section of a spinal segment and the embodiment of the invention drawn in FIG. 10A. The invention was used to treat a vertical aperture in the AF. The invention treats apertures similar to those treated in the embodiment of the invention drawn in FIG. 6D, but does not require welding technology. In alternative embodiments of the invention as well as other embodiments of the invention taught in this application and my co-pending application U.S. patent application Ser. No. 12/263,753, more or fewer of the intra-aperture components 1002 may be used, and/or different components could be substituted from other embodiments of the invention or deleted. For example, the intra-aperture components 1004 in this embodiment of the invention could be deleted and the anti-adhesion component taught in FIG. 8F added to the device.

Figure 11A:
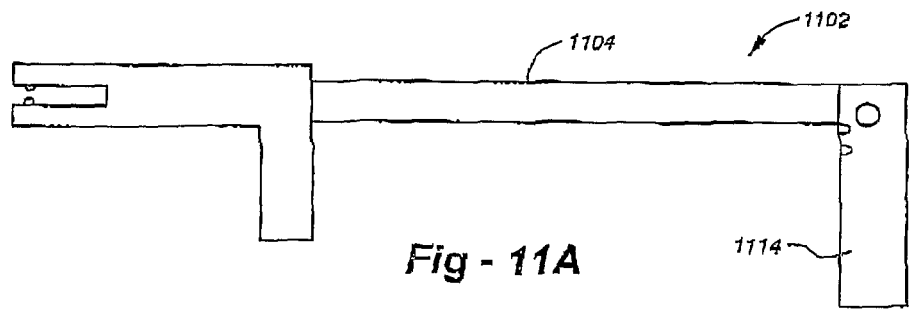
FIG. 11A is a lateral view of an alternative embodiment of the invention drawn in FIG. 3A.

FIG. 11A is a lateral view of an alternative embodiment of the invention drawn in FIG. 3A. The instruments drawn in this embodiment of the invention and the embodiment drawn in FIG. 3A are preferably made of metal and plastic. The instrument is used to pass flexible longitudinal fixation components through bone. For example, the instrument may be used to pass an arm of the flexible longitudinal fixation component through a vertebra as illustrated in FIG. 42 of my co-pending U.S. patent application Ser. No. 12/263,753.

Figure 11B:
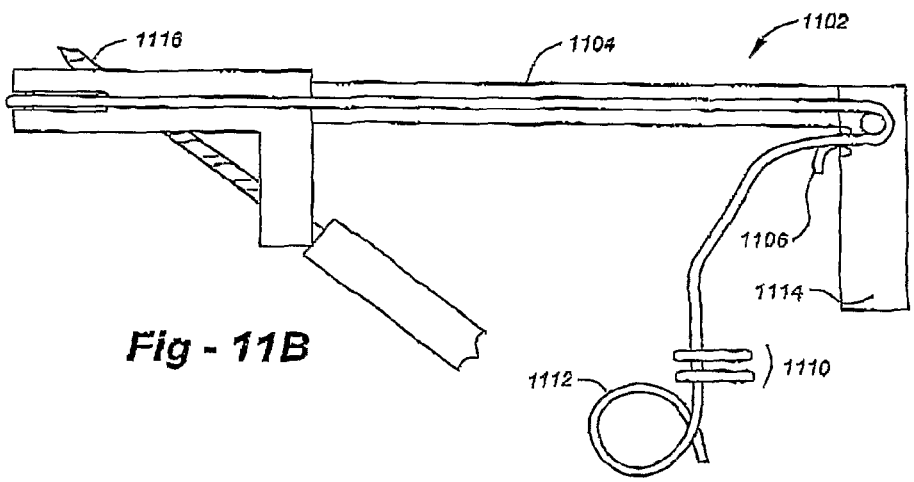
FIG. 11B is a lateral view of the embodiment of the invention drawn in FIG. 11A.

FIG. 11B is a lateral view of the embodiment of the invention drawn in FIG. 11A. The proximal and distal portions of a first arm of a flexible longitudinal fixation component were temporarily fastened to the handle of the tool. Only the tip 1106 of the distal portion of first arm of the flexible longitudinal fixation component is seen near the handle of the tool. A large segment of the distal portion of the first flexible longitudinal fixation component is hidden behind the shaft 1104 of the tool 1102.

The intra-aperture components 1110 and the second arm 1112 of the flexible longitudinal fixation component are seen hanging from the handle 1114 of the tool. A drill bit 1116 extends through holes in the distal portion of the tool. The first arm of the flexible longitudinal fixation component is temporarily held in a slot or recess in the distal portion of the instrument or tool. Such position prevents damaging the flexible longitudinal fixation component while the hole is drilled in bone. The L-shaped portion of the distal portion of the tool is preferably placed over the junction of vertebral endplates and the posterior portion of vertebrae. The horizontal component of the L-shaped portion of the tool is preferably 4 to 15 mm long, 3 to 8 mm wide and 1 to 4 mm thick. Such portion of the tool is preferably inserted through apertures in the AF and placed on the VEP.

The vertical portion of the L-shaped distal portion of the tool is preferably 4 to 15 mm long, 3 to 8 mm wide and 1 to 4 mm thick. Such portion of the tool is preferably placed over the posterior portion of vertebrae. The drill bit has a depth-limiting feature that stops advancement of the drill bit once the bit has passed through the hole in the horizontal portion of the L-shaped feature of the tool. For example, the shaft of the drill bit may have a larger diameter than the diameter of the hole in the vertical portion of the L-shaped feature of the tool. The feature preferably allows the tip of the drill bit advance 1 to 5 mm beyond the VEP. The drill bit is preferably 1 to 4 mm in diameter, but may be larger or smaller in other embodiments of the invention.

FIG. 11C is a lateral view of the distal end of a hook-like tool 1120. The diameter of the tool is preferably slightly smaller than the diameter of the drill bit described in FIG. 11B. For example, the diameter of the shaft of the hook-like tool could be 1 to 2 mm smaller than the diameter of the drill bit. FIG. 11D is a superior view of the distal end of the embodiment of the invention drawn in FIG. 11C. The hook portion of the tool is preferably narrower than the shaft of the tool in the direction transverse to the hook.

FIG. 11E is a lateral view of the embodiments of the invention drawn in FIGS. 11B and 11C. The hook-like tool was inserted into the hole drilled through bone. The shaft of the hook-like tool has a depth-limiting feature, such as a widened area. The depth-limiting feature enables the hook to pass beyond the flexible longitudinal fixation component.

FIG. 11F is a lateral view of the embodiment of the invention drawn in FIG. 11E. Tension was applied to the distal and proximal portions of the first arm of the flexible longitudinal fixation component to advance the flexible longitudinal component in a proximal direction within the slot at the tip of the horizontal portion of the L-shaped feature in the tool. The distal portion of the first arm of the flexible longitudinal fixation component was then released from the handle of the tool. FIG. 11G is a lateral view of the embodiment of the invention drawn in FIG. 11F. The hook-like tool was pulled through the holes in the tool and the hole in the bone. Such action pulls the distal portion of the first arm of the flexible longitudinal fixation component through the bone.

Figure 11H:
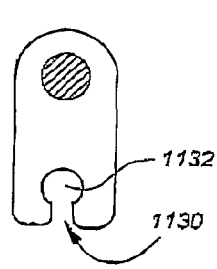
FIG. 11H is a view of the proximal end of the vertical portion of the L-shaped feature of the tool.

FIG. 11H is a view of the proximal end of the vertical portion of the L-shaped feature of the tool. A cross section of the shaft of the tool is seen near the top of the drawing. The slot 1130 in the circular opening 1132 in the vertical portion of the L-shaped feature in the tool enables the flexible longitudinal fixation component to escape from the tool.

Figure 11I:
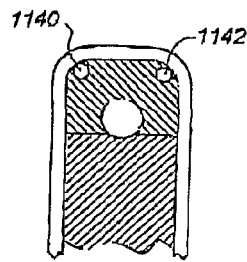
FIG. 11I is a superior view of a transverse cross section through the horizontal portion of the L-shaped feature of the tool and a portion of the first arm of the flexible longitudinal fixation component.

FIG. 11I is a superior view of a transverse cross section through the horizontal portion of the L-shaped feature of the tool and a portion of the first arm of the flexible longitudinal fixation component. The tool has features, such as projections 1140, 1142, that hold the flexible longitudinal fixation component in a first position near the distal portion of the tool. Such position prevents damaging the flexible longitudinal fixation component by the drill bit.

Figure 11J:
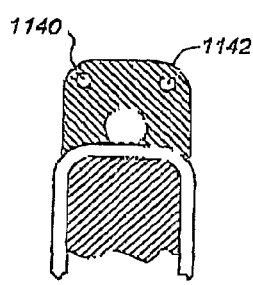
FIG. 11J is a superior view of a transverse cross section of the embodiment of the invention drawn in FIG. 11I.

FIG. 11J is a superior view of a transverse cross section of the embodiment of the invention drawn in FIG. 11I. The flexible longitudinal fixation component was advanced over the hole in the tool by pulling on proximal and distal portion of the first arm of the flexible longitudinal fixation component. Such position enables capture of the flexible longitudinal fixation component with the hook-like tool.

Figure 11K:
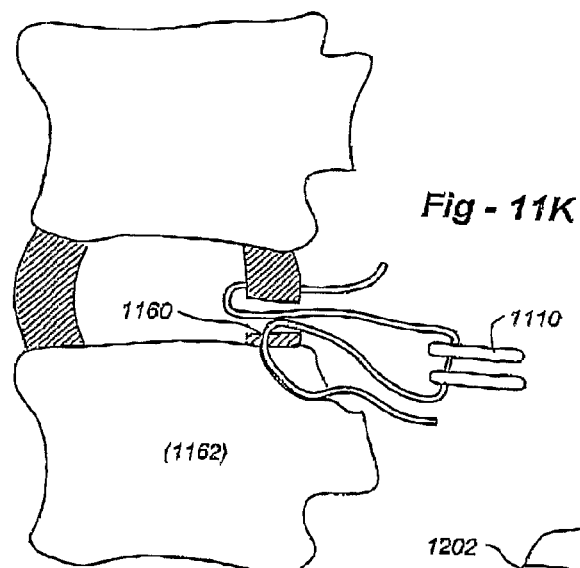
FIG. 11K is a lateral view of a spinal segment and an alternative embodiment of the invention drawn in FIG. 2D.

FIG. 11K is a lateral view of a spinal segment and an alternative embodiment of the invention drawn in FIG. 2D. The distal portion of the first arm of the flexible longitudinal fixation component was passed through a hole in the vertebra using the embodiment of the invention taught in FIGS. 11A-11J. The distal portion of the second arm of the flexible longitudinal fixation component was passed through AF tissue cranial to an aperture in the AF. Tension on the ends of the flexible longitudinal fixation component pulls the intra-aperture components into the aperture. The intra-aperture components 1110 cover the hole drilled 1160 through the vertebra 1162. The ends of the flexible longitudinal fixation component are preferably threaded into a vertebral fixation member (not shown), which is then impacted into the vertebra in the next step in the method. Alternatively, the ends of the flexible longitudinal fixation component could be welded together or otherwise fastened to each other.

Figure 12A:
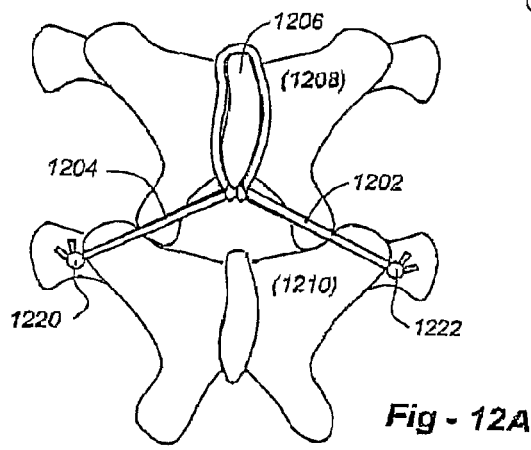
FIG. 12A is a posterior view of a spinal segment and an alternative view of the embodiment of the invention drawn in FIG. 8F.

FIG. 12A is a posterior view of a spinal segment and an embodiment of the invention which may use some of the components drawn in FIG. 8F. Two flexible longitudinal fixation components 1202, 1204 are looped around the spinous process 1206 of a first vertebra 1208 and anchored to the vertebral body of a second vertebra 1210. An anti-adhesion/connective tissue ingrowth sleeve, similar to the embodiment of the sleeve drawn in FIG. 26B of my co-pending U.S. patent application Ser. No. 12/263,753, surrounds at least a portion of each flexible longitudinal fixation element in the final device. Such sleeves were not included in the drawing to better illustrate the configuration of the flexible longitudinal fixation elements.

Figure 12B:
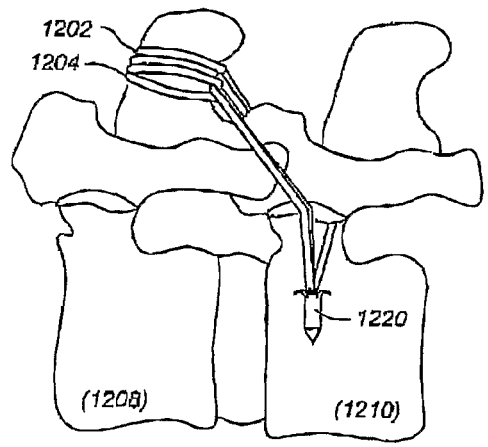
FIG. 12B is a lateral view of a partial sagittal cross section of the spinal segment and the embodiment of the invention drawn in FIG. 12A.

FIG. 12B is a lateral view of a partial sagittal cross section of the spinal segment and the embodiment of the invention drawn in FIG. 12A. The ends of each flexible longitudinal fixation element were passed through the loop of the same flexible longitudinal fixation element after such flexible component was wrapped around the spinous process. Each anchor member 1220, 1222 through which the ends of a flexible longitudinal fixation pass, was impacted through a pedicle into the vertebra body of the second vertebra.

The anchors 1220, 1222 are preferably impacted into the vertebrae through pilot holes in the vertebrae. The pilot holes are preferably 10 to 20 mm long and 2 to 4 mm in diameter and pass through the at least the majority of the pedicles. The anchors preferably pass through pedicles, may expand the pilot holes, and preferably lie completely within the vertebral body. As previously described the anchors, such as the Piton anchor (Tornier, Edina, Minn.) have a suture-locking component.

The flexible longitudinal fixation components are preferably made of multi-filament polyester or ultra high molecular weight polyethylene, and have a tensile strength of at least 75 lbs. in the preferred embodiment of the invention. The anchors are preferably at least 3.5 mm in diameter and 10 to 15 mm long. The ends of the flexible longitudinal fixation component are pulled at the end of the procedure to apply tension to and to shorten the flexible longitudinal fixation component proximal to the anchor. The locking feature of the anchor maintains the tension on the flexible longitudinal fixation component. The ends of the flexible longitudinal fixation components that extend from the holes in the vertebrae are cut and removed in the last step of the procedure.

Figure 12C:
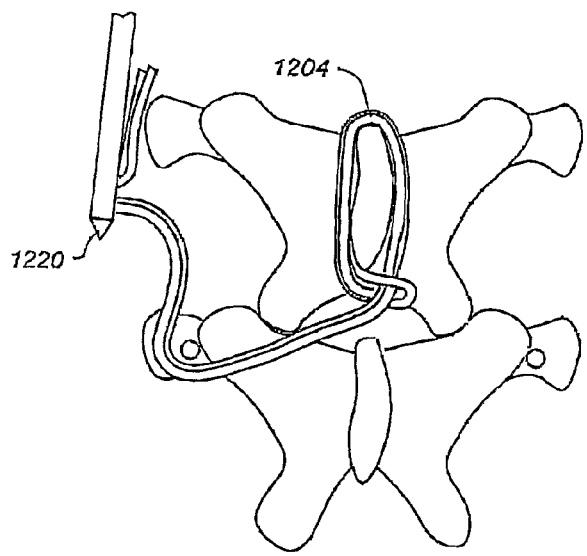
FIG. 12C is a posterior view of the spinal segment and embodiment of the invention drawn in FIG. 12A.

FIG. 12C is a posterior view of the spinal segment and embodiment of the invention drawn in FIG. 12A. The drawing shows application of the first device to the spinal segment. The anchor will be inserted into the pilot hole in the next step of the procedure. The anchors could be impacted directly into the vertebrae, without pilot holes, in alternative embodiments of the invention.

Figure 12D:
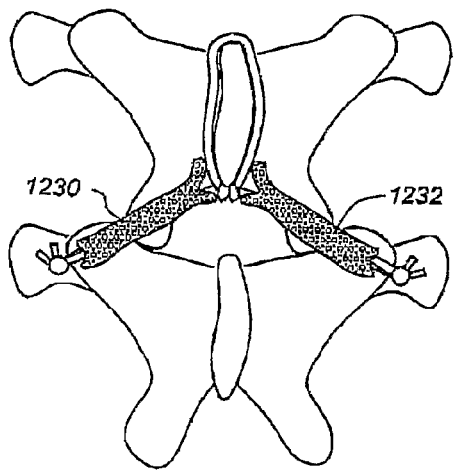
FIG. 12D is a posterior view of the spinal segment and the embodiment of the invention drawn in FIG. 12A.

FIG. 12D is a posterior view of the spinal segment and the embodiment of the invention drawn in FIG. 12A. Anti-adhesion/connective tissue ingrowth sleeves 1230, 1232 surround a portion of each flexible longitudinal fixation component. A portion of each sleeve is preferably microporous, with approximately 4 micron pores to prevent connective tissue ingrowth and a portion of each sleeve has approximately 0.5 to 2 mm pores that promote connective tissue ingrowth. Microporous portions of the sleeves preferably lie over the dura to prevent adhesions to dura and the portions of the sleeves with large pores preferably lie over the vertebrae, facet capsules, and spinal muscles. For example, such microporous sections of the sleeve are preferably located along medial and anterior portions of the sleeves and the portions of the sleeve with large pores are preferably located along the lateral and posterior portions of the sleeves.

The locations of the large and micro pores could be located in different areas of the sleeves in alternative embodiments of the invention. The sleeves are preferably made of ePTFE. Similar to the embodiment illustrated in FIG. 8F, the device is preferably fully assembled with the sleeve, before the flexible longitudinal fixation component is passed around the spinous process. Connective tissue grows into the sleeves forming ligament-like structures that also limit spinal flexion.

Figure 13A:
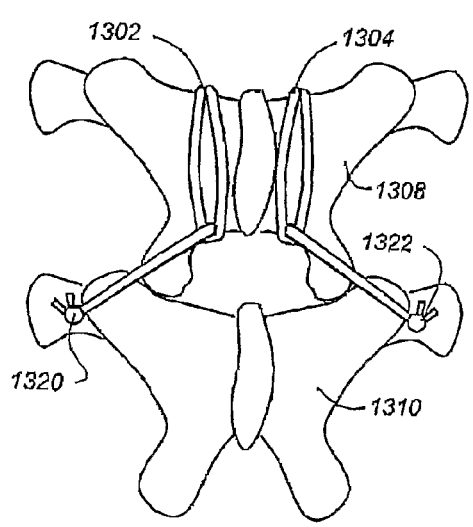
FIG. 13A is a posterior view of a spinal segment and an alternative embodiment of the invention drawn in FIG. 12A.
Figure 13B:
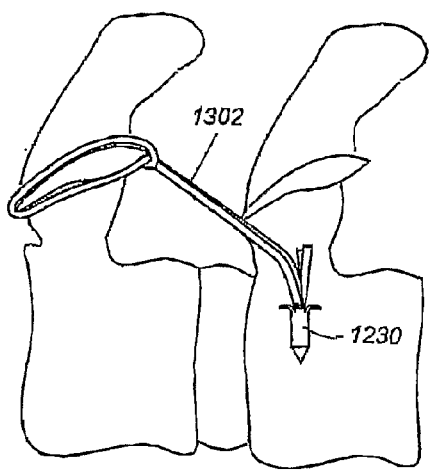
FIG. 13B is a lateral view of a partial sagittal cross section of the spinal segment and the embodiment of the invention drawn in FIG. 13A.

The devices described with respect to FIG. 12 limit spinal flexion. FIG. 13A is a posterior view of a spinal segment and an alternative embodiment of the invention drawn in FIG. 12A which also limits spinal movement FIG. 13B is a lateral view of a partial sagittal cross section of the spinal segment and the embodiment of the invention drawn in FIG. 13A. The flexible longitudinal fixation components 1302, 1304 were looped around the laminae of a first vertebra and anchored at 1320, 1322 to the body of a second vertebra. Anti-adhesion/connective tissue ingrowth sleeves, such as the sleeves drawn in FIG. 12D, preferably surround a portion of each flexible longitudinal fixation component in the fully assembled devices. Such sleeves were not included in the drawing to better illustrate the configuration of the flexible longitudinal fixation components.

Figure 14A:
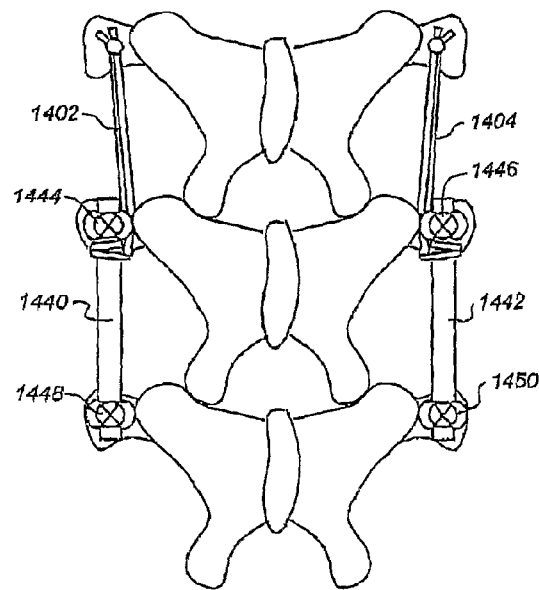
FIG. 14A is a posterior view of a spinal segment and an alternative embodiment of the invention drawn in FIG. 13A.

FIG. 14A is a posterior view of a spinal segment and an alternative embodiment of the invention drawn in FIG. 13A.

Figure 14C:
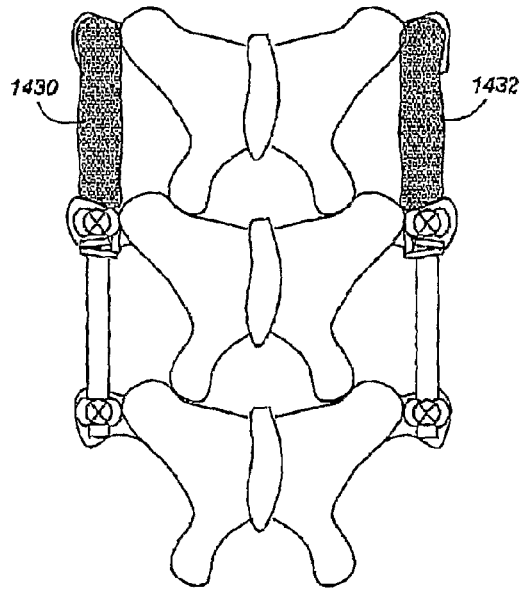
FIG. 14C is posterior view of the spinal segment and embodiment of the invention drawn in FIG. 14A.
Figure 14B:
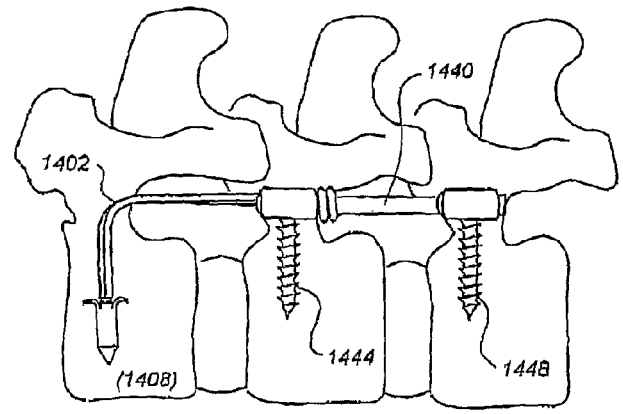
FIG. 14B is a lateral view of a partial sagittal cross section of the spinal segment and the embodiment of the invention drawn in FIG. 14A.

FIG. 14B is a lateral view of a partial sagittal cross section of the spinal segment and the embodiment of the invention drawn in FIG. 14A. Spinal rods 1440, 1442 connect pedicle screws 1444, 1446, 1448, 1450 that were placed into the two caudal vertebrae. Flexible longitudinal fixation components 1402, 1404 were looped around the spinal rods and anchored to the body of a third vertebra 1408. Anti-adhesion/connective tissue ingrowth sleeves, such as the sleeves drawn in FIG. 12D, preferably surround a portion of each flexible longitudinal fixation component in fully assembled devices. Such sleeves were not included in the drawing to better illustrate the configuration of the flexible longitudinal fixation components.

FIG. 14C is posterior view of the spinal segment and embodiment of the invention drawn in FIG. 14A. Porous sleeves 1430, 1432 surround portions of the flexible longitudinal fixation components. Such sleeves preferably have large pores, 0.5 to 2 mm in diameter, width, or length to promote connective tissue ingrowth. The sleeves do not necessarily have microporous sections. The sleeves are preferably made of polyester, polypropylene, ePTFE, or similar material.

Figure 15A:
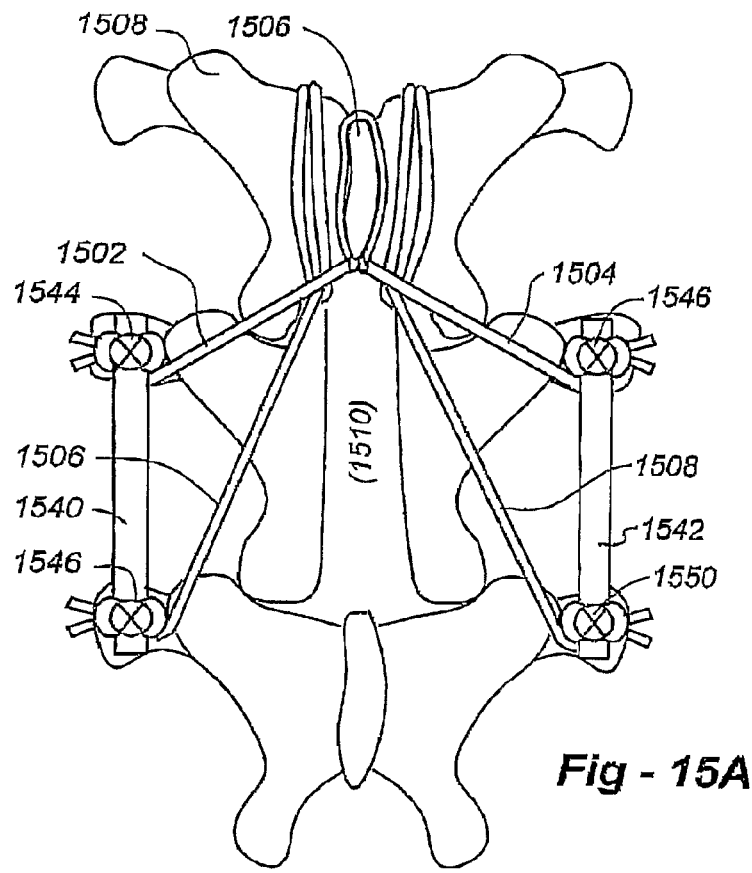
FIG. 15A is a posterior view of a spinal segment and an alternative embodiment of the invention drawn in FIG. 14C.
Figure 15B:
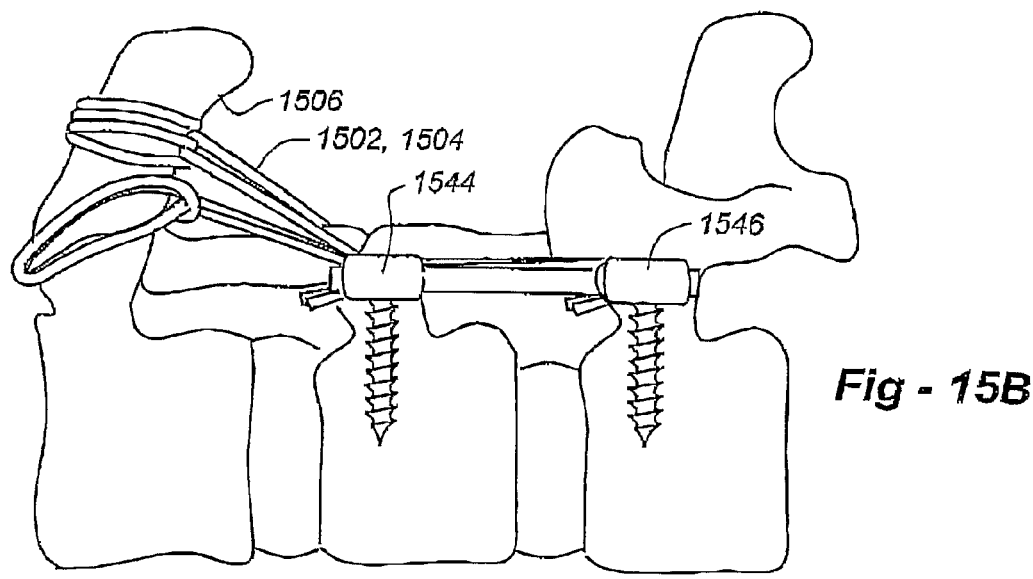
FIG. 15B is a lateral view of a partial sagittal cross section of the spinal segment and the embodiment of the invention drawn in FIG. 15A.

FIG. 15A is a posterior view of a spinal segment and an alternative embodiment of the invention drawn in FIG. 14C. FIG. 15B is a lateral view of a partial sagittal cross section of the spinal segment and the embodiment of the invention drawn in FIG. 15A. The drawings illustrate a laminectomy, surgical removal of the lamina, of the intermediate vertebrae 1510. Flexible longitudinal fixation components 1502, 1504, 1506, 1508 were looped around the spinous process and laminae 1506 of a first vertebra 1508 and anchored between the rods and pedicle screws of the second and third vertebrae. Anti-adhesion/connective tissue ingrowth sleeves, such as the sleeves drawn in FIG. 12D, preferably surround a portion of each flexible longitudinal fixation component in fully assembled devices. Such sleeves were not included in the drawing to better illustrate the configuration of the flexible longitudinal fixation components.

FIG. 15C is a view of the proximal end of a pedicle screw such as 1544 and the ends of flexible longitudinal fixation component such as 1502 drawn in FIG. 15A. The flexible longitudinal fixation component 1502 preferably passes through the central portion of the connector component of the pedicle screw. Such location assures the flexible longitudinal fixation component is compressed between the rod and the pedicle screw as the set-screw is tightened in the connector. The flexible longitudinal fixation component preferably passes from the lateral portion of the first opening for the rod in the connector portion of the screw to the medial portion of the second opening for the rod in the connector portion of the screw. The flexible longitudinal fixation component most preferably passes from the medial portion of the caudal opening for the rod in the connector portion of the screw to the lateral portion of the cranial opening for the rod in the connector portion of the screw. The edges of the connector component are preferably rounded to prevent cutting of the flexible longitudinal fixation component.

FIG. 15D is an exploded lateral view of the embodiment of the invention drawn in FIG. 15C. The arms of the flexible longitudinal fixation component 1502 pass between the rod such as 1540 and the connector portion 1544 of the pedicle screw. Set screw 1560 forces rod 1540 against the arms of the flexible longitudinal fixation component 1502, which are forced against pedicle screw 1544. FIG. 15E is lateral view of the embodiment of the invention drawn in FIG. 15D in assembled form.

Figure 16:
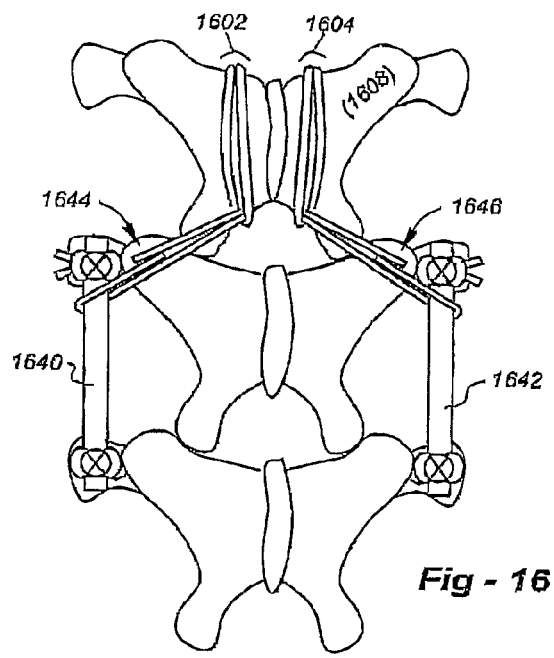
FIG. 16 is a posterior view of a spinal segment and an alternative embodiment of the invention drawn in FIG. 15A.

FIG. 16 is a posterior view of a spinal segment and an alternative embodiment of the invention drawn in FIG. 15A. Flexible longitudinal fixation components 1602, 1604 were looped around the laminae of a first vertebra 1608 and around rods 1640, 1642. The ends of the flexible longitudinal fixation components were then welded together at 1644, 1646. The welding systems supplied by Axya Medical (Beverly, Mass.) could be used to weld the flexible longitudinal fixation components. Anti-adhesion/connective tissue ingrowth sleeves, such as the sleeves drawn in FIG. 12D, preferably surround a portion of each flexible longitudinal fixation component in fully assembled devices. Such sleeves were not included in the drawing to better illustrate the configuration of the flexible longitudinal fixation components.

Figure 17A:
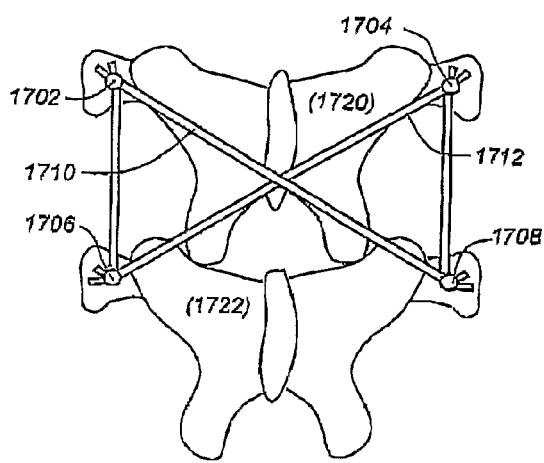
FIG. 17A is posterior view of spinal segment and an alternative embodiment of the invention drawn in FIG. 16A.

FIG. 17A is posterior view of spinal segment and an alternative embodiment of the invention drawn in FIG. 16A. FIG. 17B is a lateral view of a partial sagittal cross section of the spinal segment and embodiment of the invention drawn in FIG. 17C. Four suture anchors 1702, 1704, 1706, 1708 fasten two flexible longitudinal fixation components 1710, 1712 to the bodies of two vertebrae 1720, 1722. Medial and lateral arms of the flexible longitudinal fixation components extend from the anchors in the cranial vertebrae. Each caudal anchor contains a medial arm of a first flexible longitudinal fixation component and a lateral arm of the second flexible longitudinal fixation component. Such configuration is similar to the invention taught in my U.S. Pat. No. 6,248,106. An anti-adhesion/connective tissue ingrowth sleeve or sleeves, such as the sleeves drawn in FIGS. 12D and 17D, preferably surround portions of each flexible longitudinal fixation component in fully assembled devices. Such sleeve or sleeves were not included in the drawing to better illustrate the configuration of the flexible longitudinal fixation components.

Figure 17D:
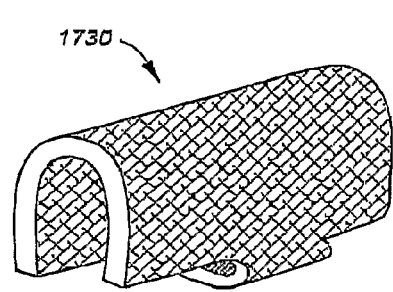
FIG. 17D is an oblique view of a connective tissue ingrowth sleeve that surrounds portions of the flexible longitudinal fixation components drawn in FIG. 17A.
Figure 17B:
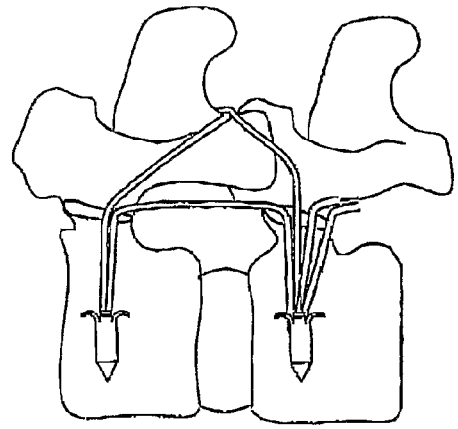
FIG. 17B is a lateral view of a partial sagittal cross section of the spinal segment and embodiment of the invention drawn in FIG. 17C.
Figure 17C:
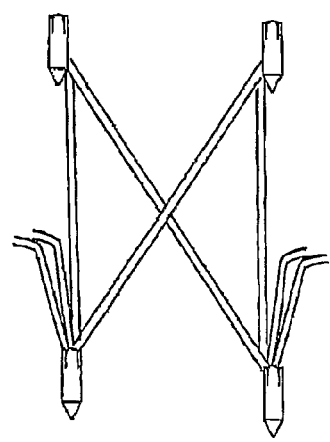
FIG. 17C is a posterior view of the embodiment of the invention drawn in FIG. 17A.

FIG. 17C is a posterior view of the embodiment of the invention drawn in FIG. 17A. The shafts of insertion tools hold the anchors in the collapsed configuration shown in the drawing. The device is preferably fully assembled as shown for immediate use by a surgeon with the flexible longitudinal fixation components passing through all the anchors and including one or more anti-adhesion/connective tissue ingrowth sleeves before the first anchor is impacted into the first vertebra.

FIG. 17D is an oblique view of a connective tissue ingrowth sleeve 1730 that surrounds portions of the flexible longitudinal fixation components drawn in FIG. 17A. The sleeve is preferably 1.5 to 5 cm tall, 0.5 to 5 cm wide, and 3 to 30 cm long. Alternatively the sleeve could be 1, 1.1, 1.2, 1.3, 1.4, 5.1, 5.2, 5.3, 5.4, 5.5, less than 1 or more than 5.5 cm tall, 0.2, 0.3, 0.4, 5.1, 5.2, 5.3, 5.4, 5.5, or more than 5.5 cm wide and 1, 1.5, 2, 2.5, 31, 32, 33, 34, or more than 34 cm long. One or more sutures pull the central portions of the walls of the component together. Alternative methods or devices, such as adhesives, could pull the central portions of the walls of the sleeve together in alternative embodiments of the invention. The inferior or anterior surface of the sleeve is preferably microporous to prevent connective tissue growth between the sleeve and the dura. The remaining portions of the sleeve preferably have 0.5 to 2 mm pores to promote connective tissue ingrowth from the spinal ligaments, bone, and muscles. The sleeve is preferably made of ePTFE. Alternatively, the entire sleeve may have 0.5 to 2 mm pores and could be made of polyester, polypropylene, or similar material.

FIG. 17E is a view of the end of the component drawn in FIG. 17D. FIG. 17F is a lateral view of the component drawn in FIG. 17D. The inferior- or anterior-most portion of the component is preferably 1.5 to 10 cm long.

FIG. 17G is a posterior view of a spinal segment and the embodiments of the invention drawn in FIGS. 17A and 17D. The medial arms of the flexible longitudinal fixation components preferably pass through the lumen of the sleeve. The sleeve is preferably inserted over the flexible longitudinal fixation components before the anchors are impacted into the vertebrae. Separate ingrowth sleeves could also surround portions of the lateral arms of the flexible longitudinal fixation components in alternative embodiments of the invention.

FIG. 17H is a lateral view of a partial sagittal cross section of a spinal segment and the embodiment of the invention drawn in FIG. 17G. Sutures 1740, 1742, 1744 were passed through the native interspinous ligaments 1750, which attach to vertebrae adjacent to the vertebrae with the device and the sutures pass through the sleeve. The sleeve 1730 serves as a scaffold for connective tissue to grow between the native supraspinous and interspinous ligaments caudal and cranial to the device. The dimensions of the sleeve preferably provide as much or more surface area for tissue ingrowth as the surface area of portions of native interspinous and supraspinous ligaments removed during surgical procedures to the spinal segment.

FIG. 17I is lateral view of an alternative embodiment of the invention drawn in FIG. 17H. The ingrowth sleeve 1760 is smaller than the ingrowth sleeve drawn in FIG. 17H. One wall of the sleeve has micropores to prevent connective tissue ingrowth. Anchor inserters 1, 2, 3, 4 hold the anchors 1770, 1772, 1774, 1776 in the compressed shape. The anchor inserters are numbered to help surgeons place the anchors in the desired locations in the spine. A suture passes 1780 through one of the walls of the sleeve. Such suture is preferably 20 to 80 cm long and 0.5 to 1.5 mm in diameter. Alternatively, such suture could be longer, shorter, thinner, or thicker in alternative embodiments of the invention. The suture is preferably made of multiple filaments of materials such as polyester or polyethylene.

The flexible longitudinal fixation components pass through the lumen of the sleeve. The sleeve is preferably 0.8 to 4 mm tall, 1 to 6 cm wide, and 1 to 30 cm long. Alternatively, the sleeve could be 0.4, 0.5, 0.6, 0.7, 4.1, 4.2, 4.3, 4.4, less than 0.4 or more than 4.4 mm tall, 0.5, 0.6, 0.7, 0.8, 0.9, 6.1, 6.2, 6.3, 6.4, less than 0.5, or more than 6.4 cm wide and less than 1 or more than 30 cm long in alternative embodiments of the invention. The sleeve is preferably made of ePTFE. The flexible longitudinal fixation components are preferably between 70 and 120 cm long. Alternatively the flexible longitudinal fixation components could be 50, 60, 130, 140, less than 50 or more than 140 cm long in alternative embodiments of the invention. The anchors contained by the $1^{st}$ and $2^{nd}$ inserters do not contain a locking feature and are preferably 2.5 to 6 mm in diameter. The anchors in the $3^{rd}$ and $4^{th}$ inserters contain a locking feature and are preferably 3.0 to 6.5 mm in diameter. As previously described 2.8 and 3.5 mm Piton anchors (Tornier, Edina, Minn.) could be used for the first and second set of anchors respectively.

Figure 17L:
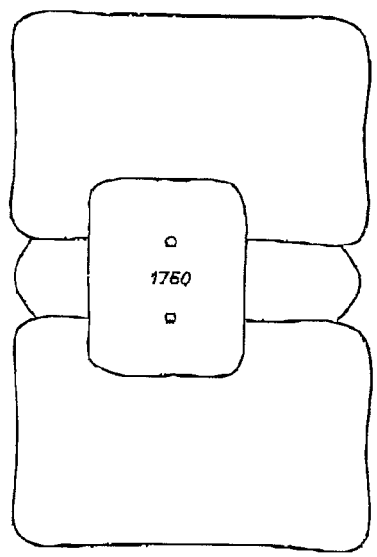
FIG. 17L is an anterior view of a spinal segment and the embodiment of the invention drawn in FIG. 17I.
Figure 17M:
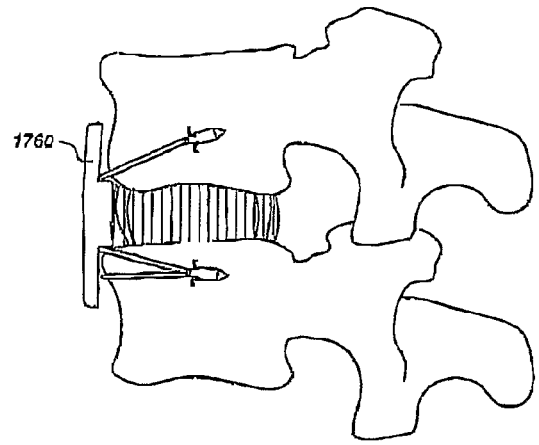
FIG. 17M is lateral view of a partial sagittal cross section of the spinal segment and the embodiment of the invention drawn in FIG. 17L.

FIG. 17J is a view of the top of the embodiment of the invention drawn in FIG. 17I. FIG. 17K is a view of the top of the embodiment of the invention drawn in FIG. 17J, however the sleeve was not included in the drawing to better illustrate the configuration of the flexible longitudinal fixation components. FIG. 17L is an anterior view of a spinal segment and the embodiment of the invention drawn in FIG. 17I. The suture was removed from the wall of the sleeve 1760 after the device was applied to the spine. FIG. 17M is lateral view of a partial sagittal cross section of the spinal segment and the embodiment of the invention drawn in FIG. 17L.

Figure 17N:
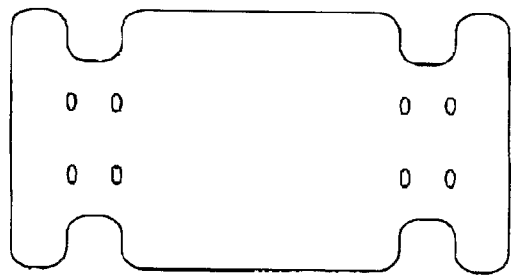
FIG. 17N is a view of the top of a novel device used to hold the components of the embodiment of the invention drawn in FIG. 17J in their proper position.

FIG. 17N is a view of the top of a novel device 1802 used to hold the components of the embodiment of the invention drawn in FIG. 17J in their proper positions.

Figure 17O:
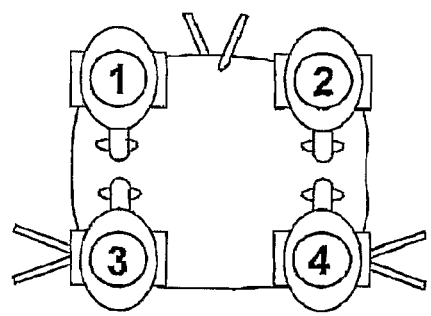
FIG. 17O is a view of the top of the embodiments of the invention drawn in FIGS. 17J and 17N.

FIG. 17O is a view of the top of the embodiments of the invention drawn in FIGS. 17J and 17N. Projections such as 1810 from the sides of the inserter handles fit between projections from the holding tool drawn in FIG. 17N to prevent rotation of the inserters relative to the holding tool. The ends of the suture that passes through the wall of the sleeve is fastened to the side of the holding tool. For example, the ends of the suture may be press fit into a notch on the side of the holding tool.

Figure 17P:
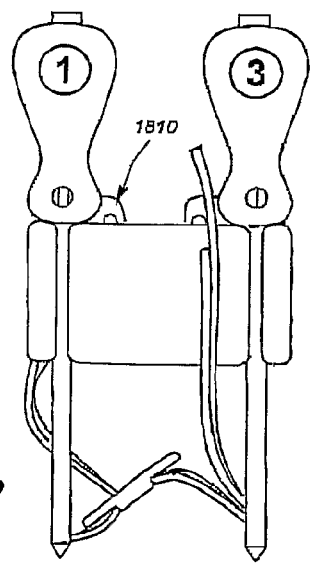
FIG. 17P is a lateral view of the embodiments of the invention drawn in FIG. 17O.

FIG. 17P is a lateral view of the embodiments of the invention drawn in FIG. 17O. The embodiment of the invention drawn in FIG. 17N is preferably 4 to 8 cm wide and long and 1 to 5 cm tall. The holding tool may be 1, 2, 3, 9, 10, 11 or more than 11 cm wide and long and 0.5, 0.75, 6, 7, less than 0.5 and more than 7 cm tall in alternative embodiments of the invention. The inserters are releasably attached to the holding tool. For example, the shafts of the inserters may be press fit into notches along the side of the holding tool. In such case, the widths of the notches in the holding tool are preferably smaller than the diameter of the shafts of the inserters. For example, the shafts of the inserters could be 4 mm in diameter and the width of the notches could be 3.9 mm, or less, wide. The holding tool is preferably made of an elastic material such as plastic, Styrofoam, polyethylene, polypropylene, or other similar material. The holding tool could fasten to other portions of the inserters, such as the handles of the inserters, in alternative embodiments of the invention.

Figure 17Q:
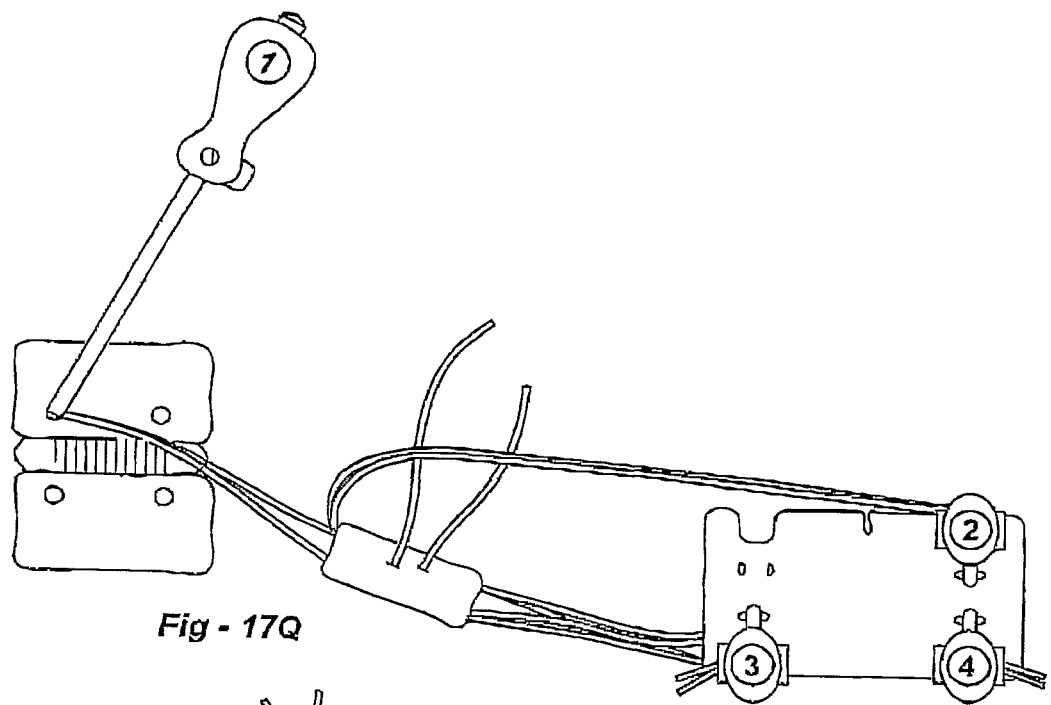
FIG. 17Q is an anterior view of a spinal segment and the embodiment of the invention drawn in FIG. 17P.

FIG. 17Q is an anterior view of a spinal segment and the embodiment of the invention drawn in FIG. 17P. The $1^{st}$ anchor was partially inserted into a pilot hole in the cranial vertebra. The holding tool holds the remaining portions of the device outside the surgical wound. The holding tool prevents twisting and tangling of the flexible longitudinal fixation components.

Figure 17R:
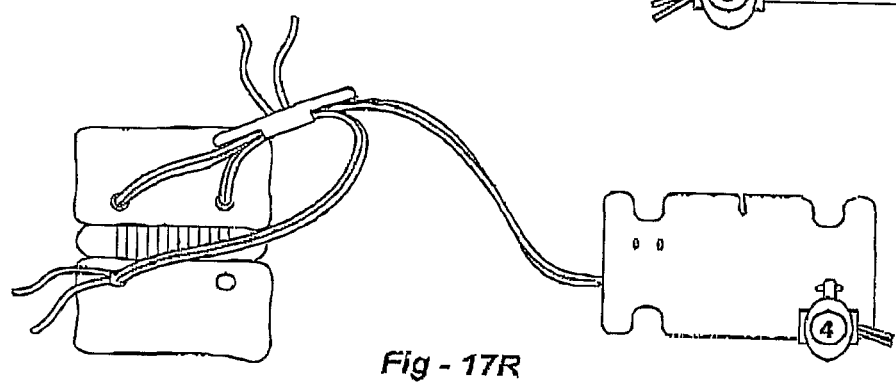
FIG. 17R is an anterior view of the spinal segment and the embodiment of the invention drawn in FIG. 17Q.

FIG. 17R is an anterior view of the spinal segment and the embodiment of the invention drawn in FIG. 17Q. The first three anchors were inserted into pilot holes in the vertebrae. The suture that passes through the sleeve is used to maneuver the sleeve. For example, tension on the suture pulls the sleeve from the $4^{th}$ pilot hole, thus improving the view of the $4^{th}$ pilot hole. The suture also holds the sleeve in a position with the anterior surface of the sleeve facing in an anterior direction. The $4^{th}$ anchor is inserted into the last pilot hole in the next step of the procedure. Then the ends of the flexible longitudinal fixation component are pulled to apply tension on the flexible longitudinal fixation components. The locking feature in the $3^{rd}$ and $4^{th}$ anchors maintains tension on the flexible fixation components. The suture is removed after insertion of the anchors in the vertebrae by pulling on one end of the suture. The ends of the flexible longitudinal fixation components are cut and removed in the last step in the procedure.

Figure 17S:
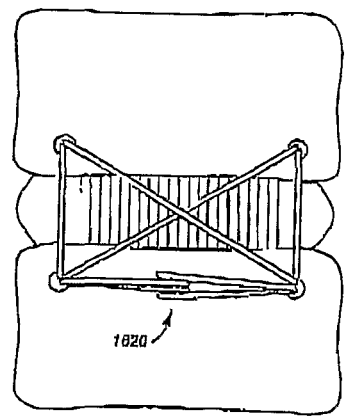
FIG. 17S is an anterior view of a spinal segment and an alternative embodiment of the invention drawn in FIG. 17L.

FIG. 17S is an anterior view of a spinal segment and an alternative embodiment of the invention drawn in FIG. 17L. The anti-adhesion/connective tissue ingrowth sleeve was not drawn to better illustrate the configuration of the flexible longitudinal fixation components. The device includes 4 anchors that do not have locking features. The ends of two flexible longitudinal fixation components were welded at 1820 over the caudal vertebra.

Figure 17T:
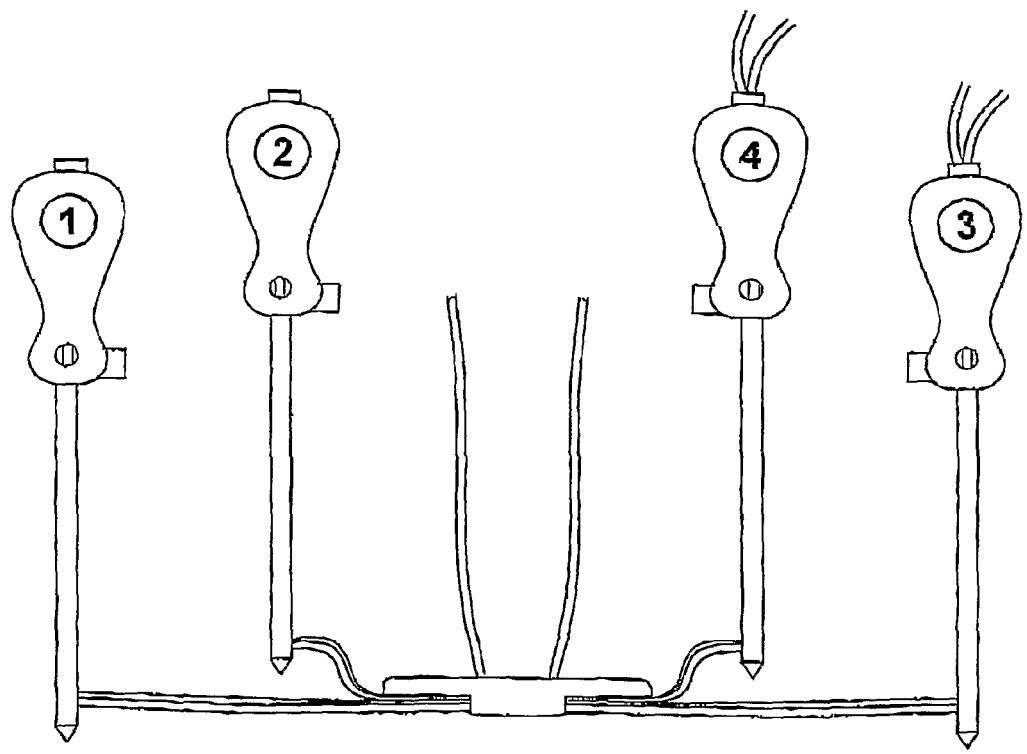
FIG. 17T is a lateral view of the embodiment of the invention drawn in FIG. 17S.

FIG. 17T is a lateral view of the embodiment of the invention drawn in FIG. 17S. The ends of a flexible longitudinal fixation component pass from anchors in inserters 1 and 2, through the anti-adhesion/connective tissue ingrowth sleeve and through anchors in inserters 3 and 4. The embodiment of the invention drawn in FIG. 17N is used to hold the components of the device in proper position.

Figure 17U:
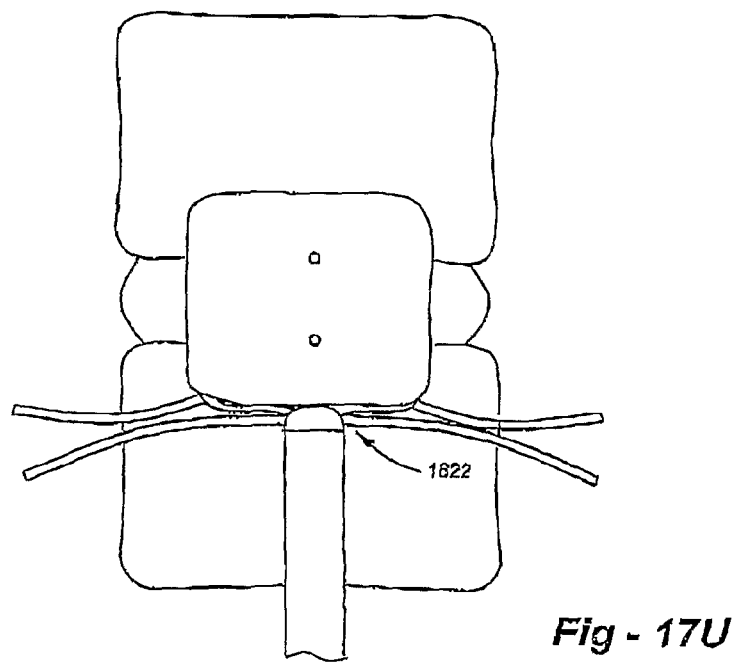
FIG. 17U is an anterior view of a spinal segment and the embodiment of the invention drawn in FIG. 17S.

FIG. 17U is an anterior view of a spinal segment and the embodiment of the invention drawn in FIG. 17S. The ends of one of the flexible longitudinal fixation components are welded at 1822 within the shaft of the welding tool shown in the bottom of the drawing. The ends of the flexible component are cut lateral to the weld in the next step of the procedure.

Figure 18A:
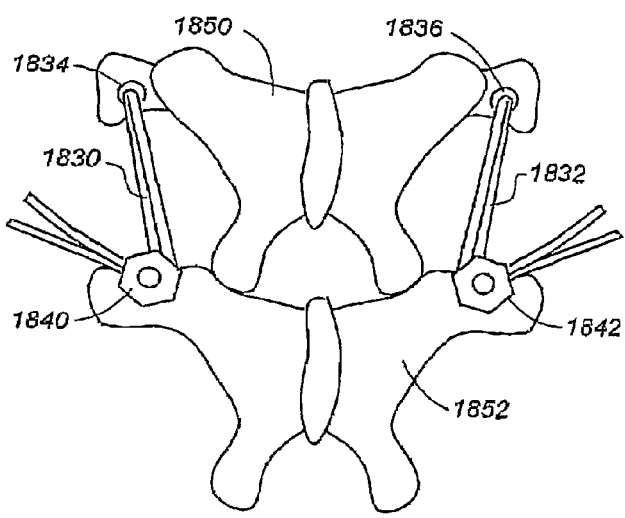
FIG. 18A is posterior view of a spinal segment and an alternative embodiment of the invention drawn in FIG. 17A.

FIG. 18A is posterior view of a spinal segment and an alternative embodiment of the invention drawn in FIG. 17A. Flexible longitudinal fixation components 1830, 1832 extend from anchors 1834, 1836 in the body of a first vertebra 1850 around threaded portions of two pedicle screws 1840, 1842. The pedicle screws are preferably passed through portions of the facet joints and anchor the ends of the flexible longitudinal fixation components to the second vertebra 1852. An anti-adhesion/connective tissue ingrowth sleeve or sleeves, such as the sleeves drawn in FIG. 12D, preferably surround portions of each flexible longitudinal fixation component in fully assembled devices. Such sleeve or sleeves were not included in the drawing to better illustrate the configuration of the flexible longitudinal fixation components.

Figure 18C:
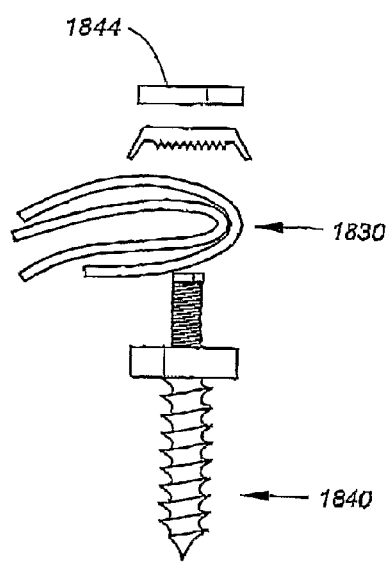
FIG. 18C is an exploded lateral view of an alternative embodiment of the invention drawn in FIG. 18B.
Figure 18B:
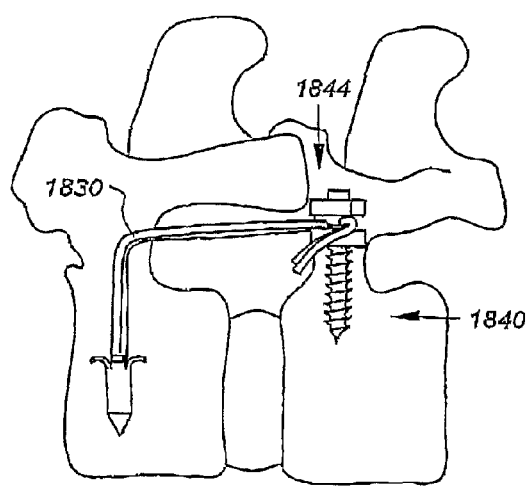
FIG. 18B is a lateral view of a partial sagittal cross section of the spinal segment and the embodiment of the invention drawn in FIG. 18A.

FIG. 18B is a lateral view of a partial sagittal cross section of the spinal segment and the embodiment of the invention drawn in FIG. 18A. The nut 1844 of the pedicle screw is tightened to compress the flexible longitudinal fixation component into a second portion of the screw. The pedicle screws causes spinal flexion and limits spinal extension, lateral bending and axial rotation. The flexible longitudinal fixation components limit spinal flexion. The invention may facilitate fusion of vertebrae.

FIG. 18C is an exploded lateral view of an alternative embodiment of the invention drawn in FIG. 18B. A washer sits between the flexible longitudinal fixation component and the nut. The distal end of the washer has projections that help capture the flexible longitudinal fixation component. Large projections around the periphery of the distal end of the washer extend over the head of the screw.

Figure 18D:
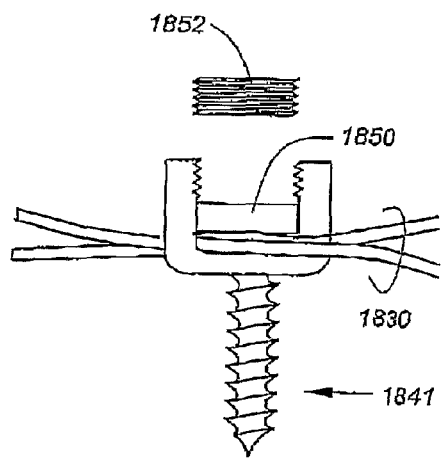
FIG. 18D is an exploded lateral view of an alternative embodiment of the invention drawn in FIG. 18C.

FIG. 18D is an exploded lateral view of an alternative embodiment of the invention drawn in FIG. 18C. Flexible longitudinal fixation components 1830 pass between a washer 1850 that is contained in the pedicle screw 1841 and a set-screw 1852. The set-screw forces the washer into the flexible longitudinal fixation component and into a second portion of the pedicle screw, thus fastening the flexible longitudinal fixation component to the pedicle screw.

Figure 19A:
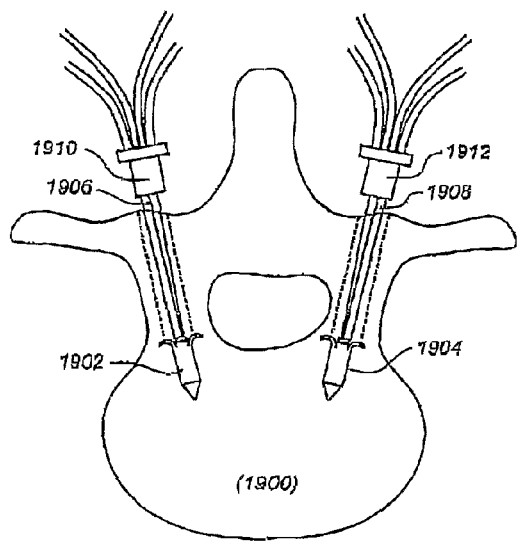
FIG. 19A is an exploded view of a partial transverse cross section of a vertebra, anchors and flexible longitudinal fixation components.

FIG. 19A is an exploded view of a partial transverse cross section of a vertebra 1900, anchors 1902, 1904 and flexible longitudinal fixation components 1906, 1908 used in preferred embodiments of the invention and sleeves 1910, 1912 that fit over the flexible longitudinal fixation components and into holes in the vertebra.

Figure 19B:
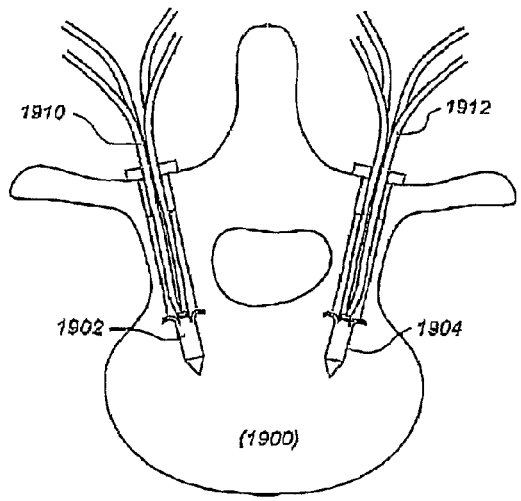
FIG. 19B is a view of the partial transverse cross section of the vertebra and the embodiment of the invention drawn in FIG. 19A.

FIG. 19B is a view of the partial transverse cross section of the vertebra and the embodiment of the invention drawn in FIG. 19A. The sleeves are preferably made of plastic, polyethylene, polypropylene, polyurethane, metal or ceramic and help prevent the flexible longitudinal fixation components from cutting into the vertebra.

Figure 20A:
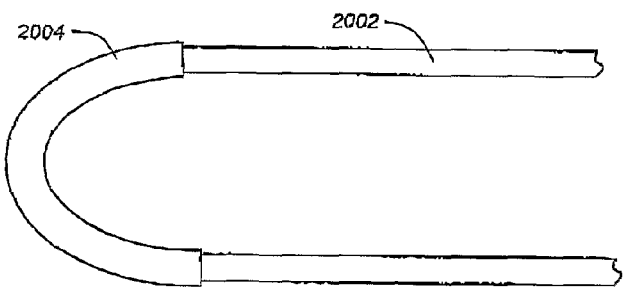
FIG. 20A is lateral view of an alternative embodiment of the flexible longitudinal fixation components drawn in preferred embodiments of the invention.

FIG. 20A is lateral view of an alternative embodiment of the flexible longitudinal fixation components 2002 drawn in preferred embodiments of the invention. The central portion of the flexible longitudinal fixation component has a U-shaped sleeve 2004 or a coating. The sleeve is preferably made of plastic, polyethylene, polypropylene, polyurethane, metal or ceramic and helps prevent abrasion between portions of the flexible longitudinal fixation components. Alternatively such portion of the flexible longitudinal fixation components could be coated with plastic, polyethylene, polypropylene, polyurethane, or other material to help prevent abrasion between portions of the flexible longitudinal fixation components.

Figure 20B:
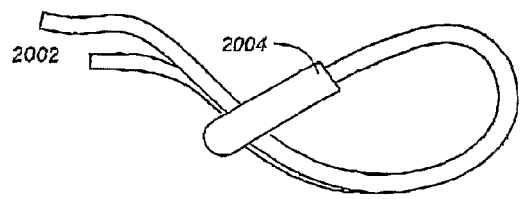
FIG. 20B is a lateral view of the embodiment of the invention drawn in FIG. 20A.

FIG. 20B is a lateral view of the embodiment of the invention drawn in FIG. 20A. The ends of the flexible longitudinal fixation component were passed over the sleeve or over the coating thus creating a lasso. The invention prevents the abrasive sides of the flexible longitudinal fixation component from sawing through itself.

Figure 21A:
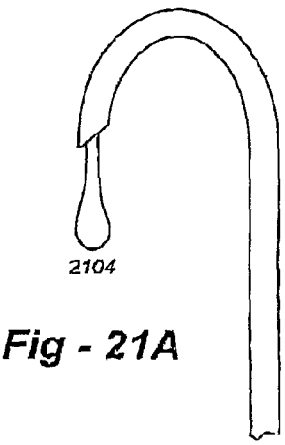
FIG. 21A is the view of the distal end of a suture-passing tool.

FIG. 21A is the view of the distal end of a suture-passing tool 2102. The U-shaped distal end of the tool is preferably 2 to 4 cm long and 0.5 to 1.5 cm wide. Alternatively, such portion of the tool could be 0.5, 1, 1.5, 4.5, 5, 5.5, less than 0.5 or more than 5.5 cm long and 0.3, 0.4, 1.6, 1.7, or more than 1.7 cm wide in alternative embodiments of the invention. A wire loop 2104 is seen extending through the lumen of the tool. The lumen of the shaft of the tool is preferably 0.5 to 3 mm in diameter. The distal tip of the tool is preferably beveled with the face of the bevel directed medially.

Figure 21B:
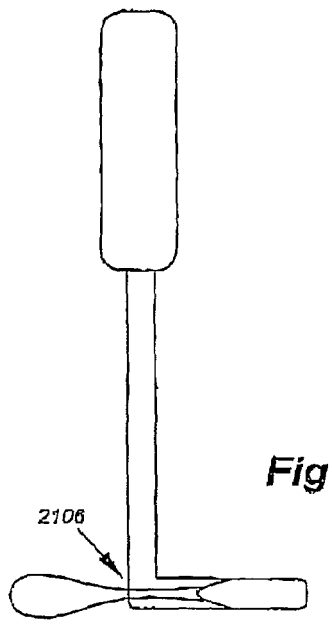
FIG. 21B is a lateral view of the embodiment of the invention drawn in FIG. 21A.

FIG. 21B is a lateral view of the embodiment of the invention drawn in FIG. 21A. The proximal end of the wire loop extends through handle 2106 of the instrument. The distal end of the same wire loop extends through the distal end of the tool. The instrument is preferable 12 to 24 cm long.

Figure 21C:
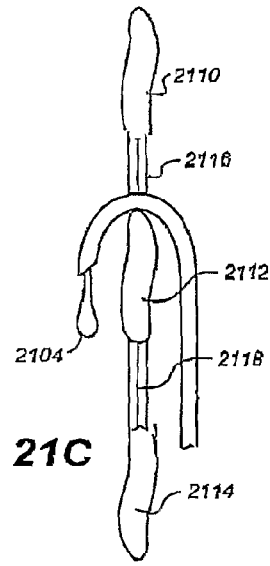
FIG. 21C is a posterior view of spinous processes, interspinous ligaments, and the embodiment of the invention drawn in FIG. 21A.

FIG. 21C is a posterior view of spinous processes 2110, 2012, 2114, interspinous ligaments 2116, 2118, and the embodiment of the invention drawn in FIG. 21A. The U-shaped end 2102 of the tool was passed around one side of spinous process 2112. A portion of flexible longitudinal fixation component (not shown) is placed into the wire loop 2104, then the proximal end of the wire loop is pulled to pull the distal end of the wire loop and a portion of the flexible longitudinal fixation component around the spinous process. The invention is used to pass flexible members around spinous processes or other structures in the spine.

Figure 22A:
FIG. 22A is a lateral view of an alternative embodiment of the invention drawn in FIG. 21A.

FIG. 22A is a lateral view of an alternative embodiment of the invention drawn in FIG. 21A. The U-shaped distal end 2202 of the tool is preferably 1 to 4 cm long and 0.5 to 1.5 cm tall. Otherwise, the tool is similar in size to the tool drawn in FIG. 21A. The distal tip of the tool is preferably beveled with the face of the bevel directed inferiorly or anteriorly. The tip of the distal end of the bevel is preferably rounded to help prevent lacerating the dura.

Figure 22B:

FIG. 22B is a lateral view of a partial sagittal cross section of three spinal laminae 2210, 2212, 2214, the ligamentum flavum 2216, 2218 between the laminae, and the embodiment of the invention drawn in FIG. 22A. The U-shaped end of the tool was passed around one side of a lamina. A portion of flexible longitudinal fixation component is placed into the wire loop (not shown), then the distal end of the wire loop and a portion of the flexible longitudinal fixation component are pulled around the lamina by pulling on the proximal end of the wire loop. The invention is used to pass flexible members around laminae or other structures in the spine.

Figure 23A:
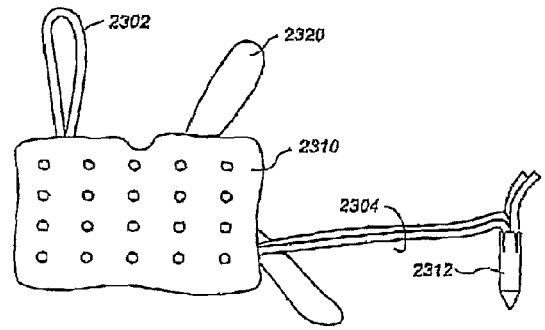

FIG. 23A is a view of the top of an alternative embodiment of the invention drawn in FIG. 12A. The loop 2302 of a flexible longitudinal fixation component 2304 extends through a porous device 2310. The ends of the flexible fixation component extend through an anchor 2312 with a locking feature. A wire loop 2320 extends through the porous device.

Figure 23B:
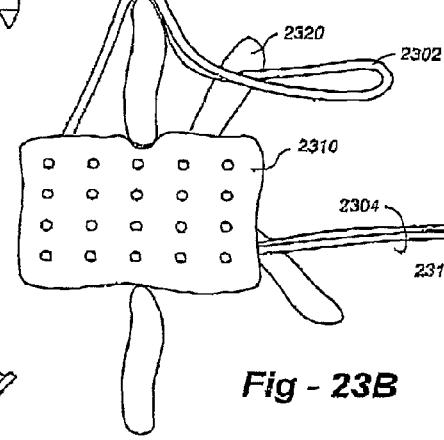

FIG. 23B is a posterior view of two spinous processes and the embodiment of the invention drawn in FIG. 23A. The flexible longitudinal fixation component loop was passed around a portion of a spinous process, then passed into one end of the wire loop. The porous device was inserted between spinous processes of adjacent vertebrae.

Figure 23C:
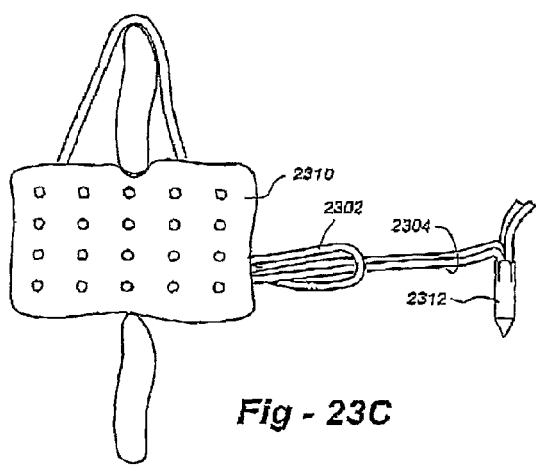

FIG. 23C is a posterior view of the spinous processes and embodiment of the invention drawn in FIG. 23B. The flexible longitudinal fixation component loop 2302 was pulled through the porous device by pulling the wire loop out of the porous device 2310. The anchor was passed through the loop in the flexible longitudinal fixation component.

Figure 23D:
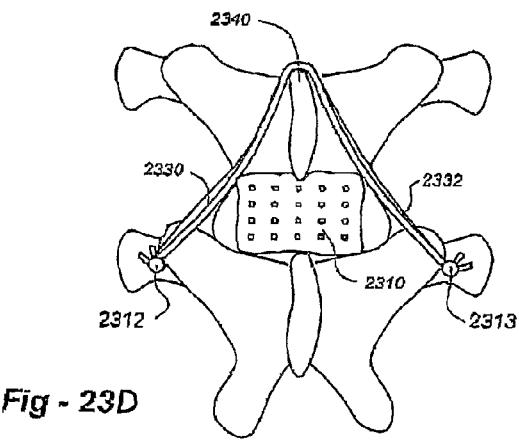

FIG. 23D is a posterior view of a spinal segment and the embodiment of the invention drawn in FIG. 23C. Two flexible longitudinal fixation components 2330, 2332 were passed around the first spinous process 2340 and through the porous device using the method taught in FIG. 23C. The anchors were then impacted into the vertebral body. Tension was applied on the ends of the flexible longitudinal fixation components followed by cutting and removing the distal ends of the flexible fixation components.

Figure 24A:
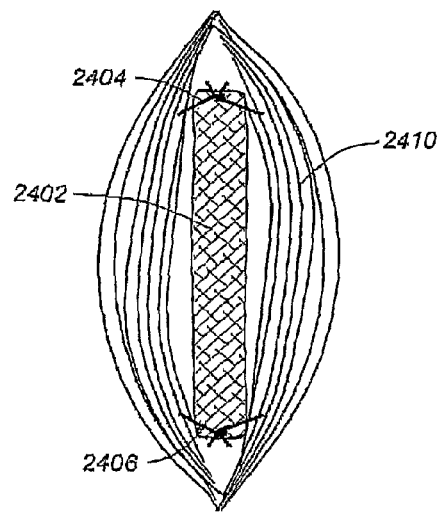

FIG. 24A is a posterior view of a portion of the spine and an alternative embodiment of the ingrowth sleeve drawn in FIG. 17D. The ends of a mesh component 2402 were sutured at 2404, 2406 to native interspinous ligaments. Retracted muscles 2410 are seen at the periphery of the device.

Figure 24C:
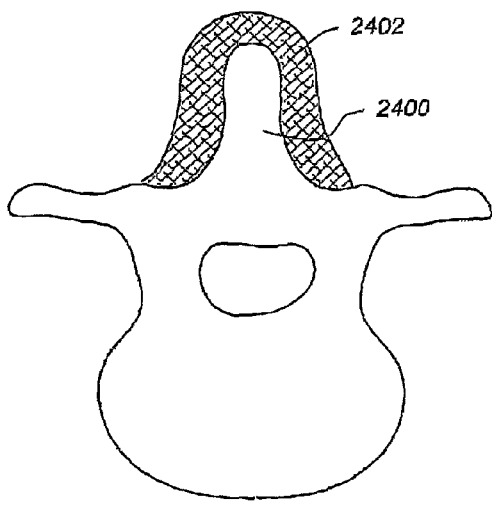
Figure 24B:
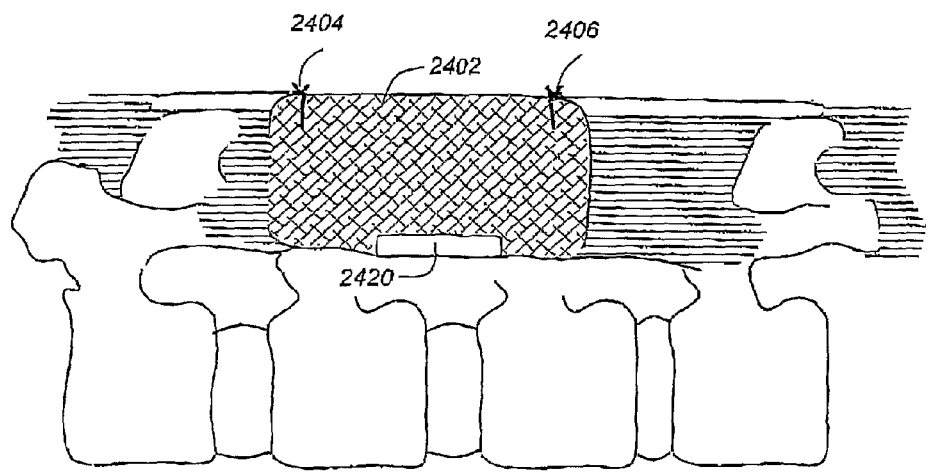

FIG. 24B is lateral view of a spinal segment and the embodiment of the invention drawn in FIG. 24A. An anti-adhesion component 2420 was fastened to the anterior side of the central portion of the mesh device 2402. For example, the mesh and anti-adhesion components could be sutured together. The anti-adhesion component, preferably made of microporous ePTFE minimizes growth of connective tissues between the mesh and the dura. The mesh is preferably made of polyester, polypropylene, nylon or similar material and preferably has pores 0.5 to 2.0 mm in diameter or width.

FIG. 24C is a view of a transverse cross section of a vertebra and the embodiment of the invention drawn in FIG. 24B. The mesh 2402 extends over the top and the sides of the spinous process 2400.

Figure 25A:
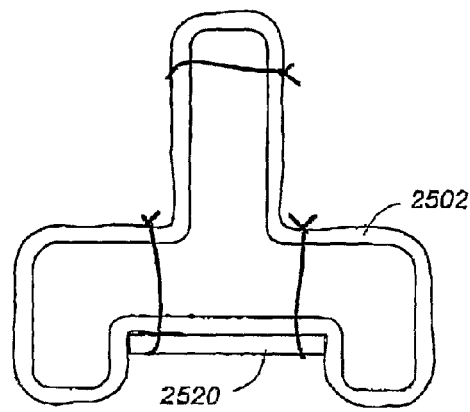
Figure 25B:
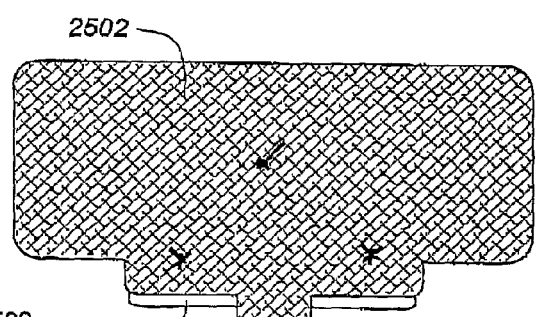

FIG. 25A is an end view of an alternative embodiment of the inventions drawn in FIGS. 17E and 24B. FIG. 25B is a lateral view of the embodiment of the invention drawn in FIG. 25A. The embodiment of the invention, like the embodiment of the invention drawn in FIG. 24B, has an anti-adhesion component 2520 fastened to the anterior surface of the connective in-growth device 2502.

Figure 25C:
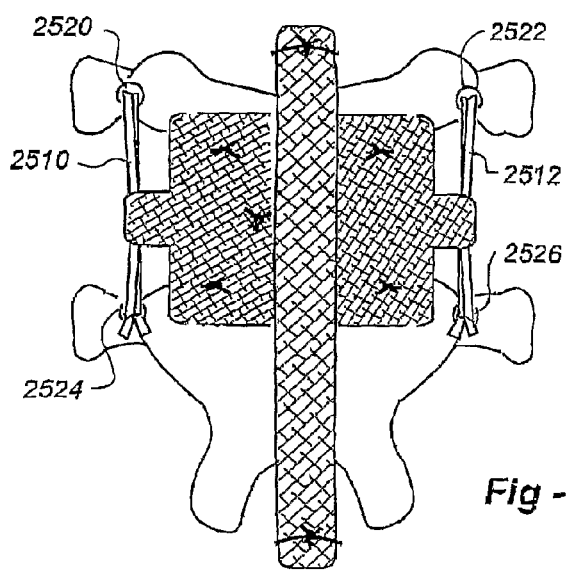

FIG. 25C is a posterior view of a spinal segment and the embodiment of the invention drawn in FIG. 25A. Flexible longitudinal fixation components 2510, 2512 pass from anchors 2520, 2522 in the first vertebra, through lumens in the lateral portions of the in-growth component and through anchors 2524, 2526 in the second vertebra. The ends of the flexible longitudinal fixation components could be passed from the anchors in the first vertebra under the skin and between muscle fibers to the second set of anchors using the invention taught in my co-pending patent application U.S. Ser. No. 11/945,998. For example, the ends of the flexible longitudinal fixation components could be manipulated under or between soft tissue structures using tool 60 of the '998 application. The ends of the flexible longitudinal fixation components could then be treaded into the second set of anchors, which are then impacted into the second vertebra.

Alternatively, as taught in the embodiment of the invention drawn in FIG. 17I, the device could be fully assembled before the anchors are impacted into the vertebrae. These embodiments of the invention (a fully assembled spinal device that restricts spinal motion in-part because such device lies outside the disc space, where the center of vertebral rotation lies), unlike prior art spinal fusion devices that must be assembled in-situ, such as rods and screws and plates and screws, is easier to insert and disrupts the spinal tissues less than such prior art motion restricting spinal devices that are assembled in-situ. The criss-cross configuration of the flexible longitudinal fixation components as shown in FIG. 17G could be used in alternative embodiments of the invention. The lateral vertical flexible longitudinal fixation components would preferably pass through the in-growth component and the criss-crossing medial flexible longitudinal fixation components would preferably pass under the in-growth component and possibly between the in-growth and anti-adhesion components in such alternative embodiments of the invention.

I claim:

1. A system for repairing a defect in the anulus fibrosis (AF) of an intervertebral disc (IVD) between upper and lower vertebral bodies, the AF having an inner surface and an outer surface, the inner surface of the AF defining an intervertebral space including nucleus pulposus (NP) tissue, the system comprising:
   a flexible longitudinal fixation component, wherein the flexible longitudinal fixation component terminates in end sections that are either attached to each other or coupled to at least one bone implant;
   at least one intra-aperture component sized and configured for positioning within a defect in the AF, the intra-aperture component comprising a proximal end, a distal portion and a plurality of holes through which the flexible longitudinal fixation component passes; wherein the intra-aperture component is folded along one or more proximal-to-distal fold lines to form one or more proximal-to-distal channels, the proximal-to-distal channels sized to facilitate the intentional initial passage of NP tissue through the intra-aperture component while preventing the extrusion of the NP tissue long term;
   wherein the distal portion of the intra-aperture component is configured to enter into an intradiscal space upon placement of the intra-aperture component within the defect in the AF; and
   wherein the flexible longitudinal fixation component is configured to pass through the holes in the intra-aperture component and outwardly through the AF on opposing sides of the defect, with one or both end sections of the flexible longitudinal fixation component crossing over the proximal end of the intra-aperture component, the holes are arranged diagonally across the intra-aperture component.

2. The system of claim 1, wherein the flexible longitudinal fixation component is a suture.

3. The system of claim 1, wherein the bone implant is a bone anchor.

4. The spinal repair system of claim 1, further including an anti-adhesion sleeve covering at least a portion of the flexible longitudinal fixation component.

5. The system of claim 1, wherein the intra-aperture component is composed of a porous mesh, allograft tissue or xenograft tissue.

6. The system of claim 1, wherein the intra-aperture component is a flexible, pad-like structure.

7. The system of claim 1, wherein the end sections of the flexible longitudinal fixation component are welded or bonded to one another over the proximal end of the intra-aperture component.

8. The spinal repair system of claim 7, further including a sleeve covering the flexible longitudinal fixation component where the ends are welded or bonded to one another.

9. The system of claim 1, wherein the plurality of holes comprise one or more reinforced holes through which the flexible longitudinal fixation component passes.

10. The system of claim 1, wherein the flexible longitudinal fixation component forms a loop through which the end sections pass before being attached to each other or coupled to at least one bone implant.

11. The system of claim 1, wherein the intra-aperture component and flexible longitudinal fixation component passing through the intra-aperture component are provided together in kit form.

12. The system of claim 1, wherein the end sections of the flexible longitudinal fixation component are coupled to a bone anchor; and
   wherein the intra-aperture component, flexible longitudinal fixation component passing through the intra-aperture component, and bone anchor to which the end sections are coupled are provided together in kit form.

13. The system of claim 1, wherein the holes are aligned transverse to the proximal-distal orientation of the intra-aperture component.

14. The system of claim 1, including a flexible longitudinal fixation component pre-coupled to at least one bone implant and provided together in kit form.

\* \* \* \* \*